US010149842B2

(12) United States Patent
Copp et al.

(10) Patent No.: US 10,149,842 B2
(45) Date of Patent: *Dec. 11, 2018

(54) SOLID FORMS OF {[5-(3-CHLOROPHENYL)-3-HYDROXYPYRIDINE-2-CARBONYL]AMINO}ACETIC ACID, COMPOSITIONS, AND USES THEREOF

(71) Applicant: Akebia Therapeutics, Inc., Cambridge, MA (US)

(72) Inventors: James Densmore Copp, Silverthorne, CO (US); Ann W. Newman, Lafayette, IN (US); Anne Luong, Mississauga (CA)

(73) Assignee: Akebia Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/994,348

(22) Filed: May 31, 2018

(65) Prior Publication Data

US 2018/0280365 A1 Oct. 4, 2018

Related U.S. Application Data

(60) Division of application No. 15/608,186, filed on May 30, 2017, now Pat. No. 9,987,262, which is a continuation of application No. 14/541,284, filed on Nov. 14, 2014, now Pat. No. 9,701,636.

(60) Provisional application No. 61/904,803, filed on Nov. 15, 2013.

(51) Int. Cl.
*C07D 213/65* (2006.01)
*A61K 31/4418* (2006.01)
*A61K 31/444* (2006.01)
*C07D 213/81* (2006.01)
*A61K 9/14* (2006.01)
*A61K 9/48* (2006.01)
*C07D 213/803* (2006.01)
*C07D 221/00* (2006.01)

(52) U.S. Cl.
CPC ............ *A61K 31/444* (2013.01); *A61K 9/14* (2013.01); *A61K 9/48* (2013.01); *C07D 213/803* (2013.01); *C07D 213/81* (2013.01); *C07D 221/00* (2013.01)

(58) Field of Classification Search
CPC .............................. C07D 213/65; A61K 31/44
USPC .......................................... 546/291; 514/346
See application file for complete search history.

(56) References Cited

U.S. PATENT DOCUMENTS 3,894,920 A 7/1975 Kondo et al.
4,016,287 A 4/1977 Ebhardt et al.
5,067,954 A 11/1991 Ilizarov
5,397,799 A 4/1995 Weidmann et al.
5,405,613 A 4/1995 Rowland
5,607,954 A 3/1997 Weidmann et al.
5,610,172 A 4/1997 Weidmann et al.
5,620,995 A 4/1997 Weidmann et al.
5,620,996 A 8/1997 Weidmann et al.
5,658,933 A 8/1997 Weidmann et al.
5,719,164 A 3/1998 Weidmann et al.
5,726,305 A 3/1998 Weidmann et al.
6,020,350 A 7/2000 Weidmann et al.
6,093,730 A 7/2000 Weidmann et al.
6,159,379 A 12/2000 Means et al.
6,420,427 B1 7/2002 Takahashi et al.
6,566,088 B1 7/2003 Zhu et al.
6,589,758 B1 7/2003 Zhu et al.
7,588,924 B2 9/2009 Evdokimov et al.
7,811,595 B2 10/2010 Kawamoto et al.
8,050,873 B2 11/2011 Evdokimov et al.
8,124,582 B2 2/2012 Guenzler-Pukall et al.
8,323,671 B2 12/2012 Wu et al.
8,343,952 B2 1/2013 Kawamoto et al.
8,512,972 B2 8/2013 Evdokimov et al.
8,530,404 B2 9/2013 Seeley et al.
8,598,210 B2 12/2013 Kawamoto et al.
8,722,895 B2 5/2014 Kawamoto et al.
8,865,748 B2 12/2014 Shalwitz et al.
8,940,773 B2 1/2015 Kawamoto et al.
9,145,366 B2 9/2015 Lanthier et al.
9,598,370 B2 3/2017 Kawamoto et al.
9,701,636 B2 7/2017 Copp et al.
9,776,969 B2 10/2017 Lanthier et al.
9,987,262 B2 6/2018 Copp et al.
2002/0192737 A1 12/2002 Kaelin, Jr. et al.
2003/0153503 A1 8/2003 Klaus et al.
2003/0176317 A1 9/2003 Guenzler-Pukall et al.
2004/0235082 A1 11/2004 Fourncy et al.
2004/0254215 A1 12/2004 Arend et al.
2006/0142389 A1 6/2006 Aurell et al.
2006/0276477 A1 12/2006 Klaus et al.
2007/0105899 A1 5/2007 Suzuki et al.
2007/0154482 A1 7/2007 Sukhatme et al.
2007/0213335 A1 9/2007 Fitch et al.
(Continued)

FOREIGN PATENT DOCUMENTS

CA 2098158 6/1993
CA 2253282 11/1997
(Continued)

OTHER PUBLICATIONS

U.S. Appl. No. 15/875,495, filed Jan. 19, 2018, Kawamoto et al.
(Continued)

Primary Examiner — Charanjit Aulakh
(74) Attorney, Agent, or Firm — Proskauer Rose LLP; Fangli Chen

(57) ABSTRACT

Provided herein are solid forms comprising {[5-(3-chlorophenyl)-3-hydroxypyridine-2-carbonyl]amino}acetic acid, compositions comprising the solid forms, methods of making the solid forms and methods of their use for the treatment of various diseases and/or disorders.

20 Claims, 12 Drawing Sheets

(56) References Cited

U.S. PATENT DOCUMENTS

| | | |
|---|---|---|
| 2007/0299086 A1 | 12/2007 | Kawamoto et al. |
| 2008/0124740 A1 | 5/2008 | Evdokimov et al. |
| 2008/0213404 A1 | 9/2008 | Johnson et al. |
| 2009/0023666 A1 | 1/2009 | Gardiner et al. |
| 2009/0082357 A1 | 3/2009 | Fitch et al. |
| 2010/0331303 A1 | 12/2010 | Kawamoto et al. |
| 2010/0331374 A1 | 12/2010 | Wu et al. |
| 2011/0077400 A1 | 3/2011 | Lobben et al. |
| 2012/0282627 A1 | 11/2012 | Evdokimov et al. |
| 2012/0309977 A1 | 12/2012 | Lanthier et al. |
| 2012/0329836 A1 | 12/2012 | Marsh et al. |
| 2013/0203816 A1 | 8/2013 | Kawamoto et al. |
| 2013/0245076 A1 | 9/2013 | Kawamoto et al. |
| 2014/0045899 A1 | 2/2014 | Kawamoto et al. |
| 2014/0057892 A1 | 2/2014 | Kawamoto et al. |
| 2015/0119425 A1 | 4/2015 | Kawamoto et al. |
| 2015/0141467 A1 | 5/2015 | Copp et al. |
| 2015/0361043 A1 | 12/2015 | Lanthier et al. |
| 2016/0009648 A1 | 1/2016 | Kawamoto et al. |
| 2016/0143891 A1 | 5/2016 | Shalwitz et al. |
| 2016/0214939 A1 | 7/2016 | Hanselmann et al. |
| 2016/0339005 A1 | 11/2016 | Shalwitz et al. |
| 2017/0189387 A1 | 7/2017 | Kawamoto et al. |
| 2017/0258773 A1 | 9/2017 | Copp et al. |
| 2017/0362178 A1 | 12/2017 | Lanthier et al. |
| 2018/0065933 A1 | 3/2018 | Hanselmann et al. |
| 2018/0092892 A1 | 4/2018 | Smith et al. |

FOREIGN PATENT DOCUMENTS

| | | |
|---|---|---|
| EP | 0650960 | 5/1995 |
| EP | 0650961 | 5/1995 |
| JP | H09221476 | 8/1997 |
| JP | 2001-48786 | 2/2001 |
| JP | A-2003-519698 | 6/2003 |
| JP | 2007-194072 | 8/2007 |
| JP | A-2009-541486 | 11/2009 |
| TW | 201002682 A1 | 1/2010 |
| WO | WO 2006/138511 | 12/1916 |
| WO | WO 1997/041103 | 11/1997 |
| WO | WO 1997/044333 | 11/1997 |
| WO | WO 1999/048870 | 11/1999 |
| WO | WO-2001/51919 A2 | 7/2001 |
| WO | WO 2002/074980 | 9/2002 |
| WO | WO 2002/074981 | 9/2002 |
| WO | WO 2002/083688 | 10/2002 |
| WO | WO 2003/028663 | 4/2003 |
| WO | WO 2003/032972 | 4/2003 |
| WO | WO 2003/049686 | 6/2003 |
| WO | WO 2003/053997 | 7/2003 |
| WO | WO 2006/114213 | 11/2006 |
| WO | WO 2007/047194 | 4/2007 |
| WO | WO 2007/070359 | 6/2007 |
| WO | WO 2007/082899 | 7/2007 |
| WO | WO 2007/084667 | 7/2007 |
| WO | WO 2007/088571 | 8/2007 |
| WO | WO 2007/103905 | 9/2007 |
| WO | WO 2007/136990 | 11/2007 |
| WO | WO 2007/150011 | 12/2007 |
| WO | WO 2008/002576 | 1/2008 |
| WO | WO-2008/002576 A2 | 1/2008 |
| WO | WO 2008/089051 | 7/2008 |
| WO | WO 2008/089052 | 7/2008 |
| WO | WO 2008/130508 | 10/2008 |
| WO | WO 2008/130527 | 10/2008 |
| WO | WO 2008/137060 | 11/2008 |
| WO | WO 2008/144266 | 11/2008 |
| WO | WO 2009/019656 | 2/2009 |
| WO | WO 2009/037570 | 3/2009 |
| WO | WO 2009/039321 | 3/2009 |
| WO | WO 2009/039323 | 3/2009 |
| WO | WO 2007/038571 | 4/2009 |
| WO | WO 2009/043093 | 4/2009 |
| WO | WO 2009/049112 | 4/2009 |
| WO | WO 2009/067790 | 4/2009 |
| WO | WO 2009/070644 | 6/2009 |
| WO | WO 2009/073497 | 6/2009 |
| WO | WO 2009/073669 | 6/2009 |
| WO | WO 2009/086044 | 7/2009 |
| WO | WO 2009/086592 | 7/2009 |
| WO | WO 2009/089547 | 7/2009 |
| WO | WO 2012/170377 | 12/2012 |
| WO | WO 2012/170439 | 12/2012 |
| WO | WO 2012/170442 | 12/2012 |
| WO | WO 2013/013609 | 1/2013 |
| WO | WO 2014/200773 | 12/2014 |
| WO | WO 2015/073779 | 5/2015 |
| WO | WO 2015/112831 | 7/2015 |
| WO | WO 2016/118858 | 7/2016 |
| WO | WO 2016/153996 | 9/2016 |
| WO | WO 2016/161094 | 10/2016 |

OTHER PUBLICATIONS

"Standards of Medical Care in Diabetes—2006," Diabetes Care, 29:s4-s42 (2006).

Alesso et al., "Improving resins for solid phase synthesis: incorporation of 1-[2-(2-methoxyethoxy)ethoxy]4-vinyl-benzene" Tetrahedron: 59,7163-7169 (2003).

Altschul et al., "Gapped BLAST and PSI-BLAST: A New Generation of Protein Database Search Programs," Nucleic Acids Res., 25(27):3389-3402 (1997).

Anderson et al., "Antileukemic Activity of Derivatives of 1,2-Dimethyl-3,4-bis(hydroxymethyl)-5-phenylpyrrole Bis(N-methylcarbamate)" J. Med. Chem.: vol. 22(8). 977-980 (1979).

Annex et al., "Growth Factor-Induced Therapeutic Angiogenesis in the Heart: Protein Therapy," Cardiovascular Research, 65(3):649-655 (2005).

Ardelt et al. "Estradiol Regulates Angiopoietin-1 mRNA Expression Through Estrogen Receptor-α in a Rodent Experimental Stroke Model," Stroke, 36:33 Jul. 3, 2011 (2005).

Auerbach et al., "Angiogenesis Assays: A Critical Overview." Clinical Chemistry. 49:32-40 (2003).

Barany et al., "Solid-phase Peptide Synthesis: A Silver Anniversary Report" Int. J. Peptide Protein Res., 30(6):705-739 (1987).

Bartlett et al., "Molecular Recognition in Chemical and Biological Problems," Special Pub., Royal Chem. Soc., 78, 182-196 Caveat: A Program to Facilitate the Structure-derived Design of Biologically Active Molecules (Apr. 1989).

Bohm, "The Computer Program LUDI: A New Method for the Novo Design of Enzyme Inhibitors," J. Computer-Aided Molecular Design, 6:61-78 (1992).

Branden et al., "Introduction to Protein Structure Second Edition," Garland Publishing. Inc., New York, 1999, pp. 374-375.

Brittain et al., "Polymorphism in Pharmaceutical Solids". Drugs and the Pharmaceutical Sciences. 2009, vol. 192, p. 334.

Burger, 1991, Isosterism and biososterism in drug design, Progress in Drug Research, Birkhauser Verlag.

Bussolino, "Molecular Mechanisms of Blood Vessel Formation" Trends Biochem. Sci., 22(7):251-256 (1997).

Catrina et al., 2004, "Hyperglycemia Regulates Hypoxia-Inducible Factor-1a Protein Stability and Function," Diabetes 53:3226-3232.

Cheeseright, 2009, "The Identification of Bioisosteres as Drug Development Candidates", Innovations in Pharmaceutical Technology, issue 28.

Cunliffe et al., "Novel Inhibitors of Prolyl 4-Hydroxylase. 3. Inhibition by the Substrate Analogue N-Oxaloglycine and Its Derivatives." J. Med. Chem. 35:2652-2658 (1992).

Elson et al., "Induction of Hypervascularity Without Leakage or Inflammation in Transgenic Mice Overexpressing Hypoxia-Indicible Factor-1α," Genes & Dev., 15:2520-2532 (2001).

European Patent Office, Interlocutory Decision in Opposition Proceedings, dated May 3, 2013, 76 pages.

European Patent Office, Minutes of the Oral Proceedings Before the Opposition Division, dated May 3, 2013, 6 pages.

Flower, "Modelling G-protein-coupled receptors for drug design," Biochimica et Biophysica Acta, 1422:207-234(1999).

(56) References Cited

OTHER PUBLICATIONS

Folkman et al., "Tumor Angiogenesis," The Molecular Basis of Cancer, Mendelsohn et al., eds., W.B. Saunders. Chapter 10, pp. 206-232 (1995).
Franklin et al., "Approaches to the Design of Anti-Fibrotic Drugs," Biochem. Soc. Trans., 19(4):812-5 (Nov. 1991).
Gaunt, 1998, "Rational Design of Benzyl-Type Protecting Groups Allows Sequential Deprotection of Hydroxyl Groups by Catalytic Hydrogenolysis", 63(13): 4172-4173.
Goodford, "A Computational Procedure for Determining Energetically Favorable Binding Sites on Biologically Important Macromolecules," J. Med. Chem., 28(7):849-857 (1985).
Goodsell et al., "Automated Docking of Substrates to Proteins by Simulated Annealing," Proteins: Structure, Function, and Genetics, 8: 195-202 (1990).
Hardcastle et al., 2005, "Discovery of Potent Chromen-4-one Inhibitors of the DNA-Dependent Protein Kinase (DNA-PK) Using a Small-Molecule Library Approach", J. of Medicinal Chem., 48(24): 7829-7846.
Hoesksema et al., 1982, "Structure of Rubradirin", J. of American Chem. Society, 104(19): 5173-5181.
International Search Report dated May 8, 2008 for PCT/US2007/014832.
International Union of Pure and Applied Chemistry; Glossary of Class Names of Organic Compounds and Reactive Intermediates Based on Structure: Pure & D Appl. Chern., vol. 67, Nos. 8/9, pp. 1307-1375, (1995).
Ivan el al., "Biochemical purification and pharmacological inhibition of a mammalian prolyl hydroxylase acting on hypoxia-inducible factor," Proceedings of the National Academy of Science; 99(21) 13459-13464 (2002).
Ivan et al., "HIFa Targeted for VHL-Mediated Destruction by Praline Hydroxylation: Implications for 02 Sensing." Science 292, 464-468 (2001).
Ivanisevic, I. et al., "Uses of X-Ray Powder Diffraction in the Pharmaceutical Industry. Pharmaceutical Formulation & Quality", Aug./Sep. 2011, p. 32.
Jaakkola el al., "Targeting of HIF-α to the von Hippel-Lindau Ubiquitylation Complex by $O_2$-Regulated Prolyl Hydroxylation," Science 292, 468-472 (2001).
Jones el al., "Molecular Recognition of Receptor Sites Using a Genetic Algorithm with a Description of Desolvation," J. Mol. Biol., 245:43-53 (1995).
Kaelin, "Proline Hydroxylation and Gene Expression," Annu. Rev. Biochem., 74:115-125 (2005).
Kawashima el al., Suppressive effect of quinolinic acid and hippuric acid on bone marrow erythroid growth and lymphocyte blast formation in uremia, Advances in Experimental Medicine and Biology, (1987), vol. 223, p. 69-72.
Krantz, "Erythropoietin," Blood, 77:419-434 (1991).
Kuntz et al., A Geometric Approach to Macromolecule-Ligand Interactions, J. Mol. Biol., 161:269-288 (1982).
Langsetmo, 2006, "Inhibition of HIF-Prolyl Hydroxylases with FG-4539 is Neuroprotective in a Mouse Model of Permanent Focal Ischemia," International Stroke Conference, Kissimmee Florida, Presentation No. 427.
Lee et al., "Structure of Human FIH-1 Reveals a Unique Active Site Pocket and Interaction Sites for HIF-1 and von Hippel Lindau," JBC, 278:7558-7563 (2003).
Li et al., "PR39, A Peptide Regulator of Angiogenesis," Nat Med., 6(1):49-55 (2000).
Lima and Barreiro, 2005, "Bioisosterism: A Useful Strategy for Molecular Modification and Drug Design", Current Medicinal Chemistry, 12:23-49.
Mancini et al., "Effect of Erythropoietin on Exercise Capacity in Patients with Moderate to Severe Chronic Heart Failure," Circulation, 107:294-299 (2003).
McDonough et al., "Cellular Oxygen Sensing: Crystal Structure of Hypoxia-Inducible Factor Prolyl Hydroxylase (PHD2)," PNAS, 103(26):9814-9819 (2006).

Miranker et al., "Functionality Maps of Binding Sites: A Multiple Copy Simultaneous Search Method," Proteins: Structure, Function and Genetics, 11:29-34 (1991).
Nguyen et al., "Cellular Interactions in Vascular Growth and Differentiation" Int. Review of Cytology. 204:1-48 (2001).
Nishibata et al., "Automatic Creation of Drug Candidate Structures Based on Receptor Structure. Starting Point for Artificial Lead Generation," Tetrahedron. 47( 43):8985-8990 (1991).
O'Reilly et al., "Angiostatin: A Novel Angiogenesis Inhibitor that Mediates the Suppression of Metastases by a Lewis Lung Carcinoma," Cell, 79:315-328 (1994).
O'Reilly et al., "Endostatin: An Endogenous Inhibitor of Angiogenesis and Tumor Growth," Cell, 88:277-285 (1997).
Peyssonnaux et al., "HIF-1α Expression Regulates the Bactericidal Capacity of Phagocytes," J. Clinical Invest., 115(7): 1806-1815 (2005).
Piyamongkol et al., 2010, "Amido-3-hydroxypyridin-4-ones as Iron (III) Ligands", Chemistry A European Journal, vol. 16: 6374-6381.
Qian et al., "A Randomized, Double-Blind, Placebo Controlled Trial of FG-4592 for Correction of Anemia in Subjects with Chronic Kidney Disease in China," Oral Abstract FR-ORO011, J. Am. Soc. Nephrol. 24:38A (2013).
Rahtu-Korpela, 2014, "HIF Prolyl 4-Hydroxylase-2 Inhibition Improves Glucose and Lipid Metabolism and Protects Against Obesity and Metabolic Dysfunction," Diabetes 63:3324-:3333 (2014).
Schelhass and Waldmann, 1996, "Protecting Group Strategies in Organic Synthesis". Chem. Int. Ed. Engl., 36:2056-2083.
Schoneberg et al., "Structural Basis of G Protein-Coupled Receptor Function," Molecular and Cellular Endocrinology, 151:181-193 (1999).
Search Report dated Apr. 28, 2011 for European Pat. App. No. 11000872.9.
Semenza et al., "Transcriptional Regulation of Genes Encoding Glycolytic Enzymes by Hypoxia-Inducible Factor 1," J. Biol. Chem., 269:23757-23763 (1994).
Semenza, "Regulation of Erythropoietin Production: New Insights into Molecular Mechanisms of Oxygen Homeostasis," Hematol. Oncol. Clin. North Am., 8:863-884 (1994).
Semenza, "Signal Transduction to Hypoxia-inducible Factor 1," Biochem. Pharmacol, 64:993-998 (2002).
Sexton, "Recent advances in our understanding of peptide hormone receptors and RAMPS," Current Opinion in Drug Discovery and Development, 2(5):440-448 (1999).
Sheehan, "3-Hydroxypicolinic Acid and Some of its Derivatives," J. Organic Chemistry 31(1):636-6:38 (1996).
Teicher et al., "Potentiation of Cytotoxic Cancer Therapies by TNP-470 Alone and with Other Anti-Angiogenic Agents," Int. J. Cancer, 57:920-925 (1994).
Thornber, 1979, "Isosterism and Molecular Modification in Drug Design", Progress Drug Res., vol. 37: 563-580.
Tzschucke et al., "Fluorous-Silica-Supported Perfluoro-Tagged Palladium Complexes Catalyze Suzuki Coupling in Water" Helvetica Chimica Acta: vol. 87 2882-2889 (2004).
Vickerstaffe et al., "Fully Automated Polymer-Assisted Synthesis of 1,5-Biaryl Pyrazoles," J. Comb. Chem., 2004, 6, 332-33.
Vippagunta et al., 2001, "Crystalline solids." Adv Drug Deliv Rev. 48(1):3-26.
Vincent et al., "Angiogenesis is Induced in a Rabbit Model of Hindlimb Ischemia by Naked DNA Encoding an HIF-1a/VP16 Hybrid Transcription Factor," Circulation, 102:2255-2261 (2000).
Warnecke et al., "Activation of the Hypoxia-Inducible Factor Pathway and Stimulation of Angiogenesis by Application of Prolyl Hydroxylase Inhibitors," FASEB Journal, 17: 1186-1188 (2003).
Warshakoon et al., "Design and synthesis of substituted pyridine derivatives as HIF-1alpha prolyl hydroxylase inhibitors," Bioorganic & Medicinal Chemistry Letters, 16 (2006) 5616-5620.
Wax el al., "SM-20 is a Novel20-kd Protein Whose Expression in the Arterial Wall is Restricted to Smooth Muscle," Lab. Invest., 74(4):797-808 (1996).
Weidner et al., "Tumor Angiogenesis and Metastasis—Correlation in Invasive Breast Carcinoma," New Eng. J. Med., 324(1):1-8 (1991).

(56) References Cited

OTHER PUBLICATIONS

Wright et al., "Activation of the Prolyl Hydroxylase Oxygen-Sensor Results in Induction of GLUTI, Heme Oxygenase-1, and Nitric-Oxide Synthase Proteins and Confers Protection from Metabolic Inhibition to Cardiomyocytes," J. Bio. Chem., 278(22):20235-20239 (2003).

Sutter, 2000, "Hypoxia-inducible factor 1 alpha protein expression is controlled by oxygen regulated ubiquitination that is disrupted by deletions and missense mutations", PNAS vol. 97, No. 9, pp. 4748-4753.

International Search Report and Written Opinion dated Jan. 29, 2015 for International Application No. PCT/US14/65631.

Extended European Search Report dated Mar. 24, 2017 for European Pat. App. No. 14861394.6.

Seymour et al., 2011, "Decision T 0777/08 of the Boards of Appeal of the European Patent Office", retrieved from the internet: http://www.epo.org/law-practice/case-law-appeals/pdf/t080777ex1.pdf [retrieved Dec. 19, 2017].

"Hippuric acid sodium salt", Science Lab.com: Chemicals & Laboratory Equipment (http://web.archive.org/web/20041107121553/http://www.sciencelab.com/page/S/PVAR/10415/SLH2620 accessed Mar. 11, 2010).

Byrn et al., 1995, "Pharmaceutical Solids: A Strategic Approach to Regularity Considerations", Pharmaceutical Research, 12(7): 945-954.

Redondo et al., 2000, "Vascular endothelial growth factor (VEGF) and melanoma. N-Acetylcysteine downregulates VEGF Production in vitro", Cytokine, 12(4):374-378.

Dranoff, 2003, "GM-CSF-secreting melanoma vaccines", Oncogene, 22:3188-3192.

U.S. Appl. No. 16/119,146, filed Aug. 31, 2018, Kawamoto et al.

Caira et al., "Crystalline Polymorphism of Organic Compounds", Topics in Current Chemistry, vol. 198: 163-208 (1998).

Kawaguchi et al., Journal of Human Environmental Engineering, vol. 4, No. 2, 2002, pp. 310-317.

Notification No. 568 of Pharmaceutical Safety and Environmental Health Bureau, Evaluation and Licensing Division, 2001.

Pharm Stage 2007, vol. 6, No. 10, pp. 20-25 "API form screening and selection in drug discovery stage".

Pharm Stage 2007, vol. 6, No. 10, pp. 48-53 "Crystallization of Polymorphs and Pseudo-polymorphs and Its Control".

Yamano, "Approach to Crystal Polymorph in Process Research of New Drug", Journal of Society of Synthetic Organic Chemistry, Japan, 2007, vol. 65, pp. 907-913.

Non-polarised

Polarised

SOLID FORMS OF {[5-(3-CHLOROPHENYL)-3-HYDROXYPYRIDINE-2-CARBONYL]AMINO}ACETIC ACID, COMPOSITIONS, AND USES THEREOF

This application is a divisional of U.S. patent application Ser. No. 15/608,186, filed May 30, 2017, which is a divisional of U.S. patent application Ser. No. 14/541,284, filed Nov. 14, 2014, now U.S. Pat. No. 9,701,636, issued on Jul. 11, 2017, which claims the benefit of U.S. Provisional Application No. 61/904,803, filed Nov. 15, 2013, the entire contents of which are incorporated herein by reference.

1. FIELD OF THE INVENTION

Provided herein are solid forms of {[5-(3-chlorophenyl)-3-hydroxypyridine-2-carbonyl]amino}acetic acid, compositions comprising one or more solid forms, methods of making the solid forms and methods of their use for the treatment of various or symptoms thereof.

2. BACKGROUND OF THE INVENTION

The identification and selection of a solid form of a pharmaceutical Compound (I) is complex, given that a change in solid form may affect a variety of physical and chemical properties, which may provide benefits or drawbacks in processing, maintaining, storage, formulation, stability and bioavailability, among other important pharmaceutical characteristics. Potential pharmaceutical solids include crystalline solids, amorphous solids, and mixtures thereof. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (See, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, potential solid forms of a pharmaceutical Compound (I) include single-component and multiple-component solids. Single-component solids consist essentially of the pharmaceutical Compound (I) in the absence of other compounds. Variety among single-component crystalline materials may potentially arise from the phenomenon of polymorphism, wherein multiple three-dimensional arrangements exist for a particular pharmaceutical compound (See, e.g., S. R. Byrn et al., Solid State Chemistry of Drugs, (1999) SSCI, West Lafayette). The importance of discovering polymorphs was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (See S. R. Chemburkar et al., *Org. Process Res. Dev.*, (2000) 4:413-417).

Additional diversity among the potential solid forms of a pharmaceutical compound may arise from the possibility of multiple-component solids. Crystalline solids comprising two or more ionic species are termed salts (See, e.g., Handbook of Pharmaceutical Salts: Properties, Selection and Use, P. H. Stahl and C. G. Wermuth, Eds., (2002), Wiley, Weinheim). Additional types of multiple-component solids that may potentially offer other property improvements for a pharmaceutical compound or salt thereof include, e.g., hydrates, solvates, co-crystals and clathrates, among others (See, e.g., S. R. Byrn et al., Solid State Chemistry of Drugs, (1999) SSCI, West Lafayette). Moreover, multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

A new class of prolyl hydroxylase inhibitors and their use to treat or prevent diseases ameliorated by modulation of hypoxia-inducible factor (HIF) prolyl hydroxylase are described in U.S. Pat. No. 7,811,595, which is incorporated herein by reference in its entirety. The synthesis of such prolyl hydroxylase inhibitors is described in U.S. Patent Publication No. 2012/0309977, which is incorporated herein by reference in its entirety. Such compounds inhibit HIF prolyl hydroxylase, thereby stabilizing HIFα. As a consequence of stabilizing HIFα, endogenous erythropoietin (EPO) production is increased. One such compound is {[5-(3-chlorophenyl)-3-hydroxypyridine-2-carbonyl]amino}acetic acid ("Compound (I)") and methods of making the compound were disclosed in U.S. Pat. No. 7,811,595, filed Jun. 26, 2007 (See inter alia Schemes I and II and accompanying synthetic procedures in columns 15-17, and 25) and U.S. Publication 2012-0309977 (U.S. patent application Ser. No. 13/488,554), filed in Jun. 5, 2012 (See inter alia paragraphs [0254]-[267]), the entireties of each of which are incorporated by reference herein.

3. SUMMARY OF THE INVENTION

Provided herein are solid forms comprising {[5-(3-chlorophenyl)-3-hydroxypyridine-2-carbonyl]amino}acetic acid ("Compound (I)"). In certain embodiments, the solid forms may be single-component crystal forms Compound (I). In certain alternative embodiments, the solid forms may be multiple-component crystal forms, including, but not limited to, salts, co-crystals, solvates, hydrates of Compound (I). In other embodiments, the solid forms are single-component amorphous forms of the free acid of Compound (I). In other embodiments, the solid forms are multiple-component amorphous forms, including, but not limited to, salts of Compound (I). Also provided herein are pharmaceutical compositions comprising the solid forms and methods of their use for the treatment or prevention of anemia (e.g., anemia secondary to or associated with chronic kidney disease, anemia secondary to chronic heart disease, idiopathic anemia of aging, anemia of chronic disease, myelodysplastic syndrome, bone marrow fibrosis, other aplastic or dysplastic anemias, chemotherapy induced anemia (including chemotherapy for treating cancer, hepatitis C, or other chronic drug therapy that reduces bone marrow production), anemia resulting from blood loss, anemia resulting from iron deficiency, anemia resulting from vitamin B12 deficiency, sickle cell disease, or thalassemia). Certain embodiments are provided herein including solid forms of Compound (I) including, but not limited to, polymorphs of the unsolvated, free acid, salts, and other useful solid forms.

In certain embodiments, the invention relates to Form A of Compound (I):

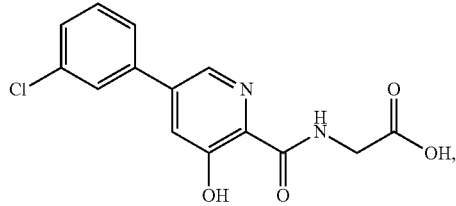

(I)

which has an X-ray powder diffraction pattern as shown in FIG. 1. In certain embodiments, Form A of Compound (I) has an X-ray powder diffraction pattern comprising one, two, three, four, or five peaks at approximately 18.1, 20.3, 22.9, 24.0, and 26.3 °2θ; and wherein the crystalline Compound (I) is substantially free of any other crystalline form of Compound (I).

In certain embodiments, Form A of Compound (I) has a peak maximum temperature in a DSC thermogram at about 175.8° C. In particular embodiments, the thermal event at about 175.8° C. is a melting event. In certain embodiments, Form A of Compound (I) melts at about 175.8° C.

In certain embodiments, Form A of Compound (I) comprises less than about 15%, less than about 10%, or less than about 5% by weight of any other crystalline Compound (I).

In certain embodiment, the invention relates to Form A of Compound (I):

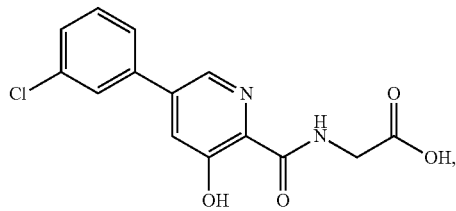

(I)

which has an X-ray powder diffraction pattern comprising one, two, three, four, or five peaks at approximately 18.1, 20.3, 22.9, 24.0, and 26.3 °2θ; and wherein the crystalline Compound (I) is substantially free of amorphous Compound (I).

In certain embodiments, Form A of Compound (I) has a peak in a DSC thermogram at about 175.8° C. In particular embodiments, the thermal event at about 175.8° C. is a melting event. In certain embodiments, the crystalline Compound (I) melts at about 175.8° C.

In certain embodiments, Form A of Compound (I) comprises less than about 15%, less than about 10% or less than about 5% by weight of amorphous Compound (I).

In certain embodiments, the invention relates to a crystalline Compound (I), such as Form A of Compound (I):

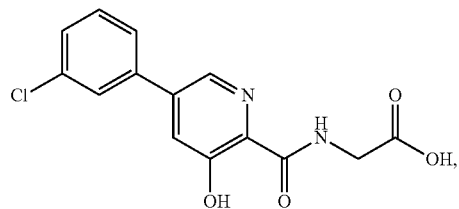

(I)

wherein the crystalline Compound (I), such as Form A of Compound (I) is substantially free of a compound of Formula (II):

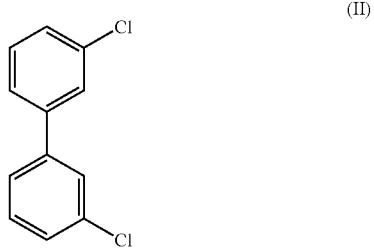 [SMILES: Clc1cccc(-c2cccc(Cl)c2)c1]

(II)

as determined by GC/MS. In certain embodiments, the crystalline compound comprises less than about 100 ppm, less than about 50 ppm, less than about 10 ppm, or less than 1 ppm of a compound of Formula (II) as determined by GC/MS. In certain embodiments, crystalline Compound (I), such as Form A of Compound (I) comprises an amount of Formula (II) that is less than a detectable amount by GC/MS.

In certain embodiments, Form A of Compound (I) has an X-ray powder diffraction pattern comprising one, two, three, four, or five peaks at approximately 18.1, 20.3, 22.9, 24.0, and 26.3 °2θ.

In certain embodiments, Form A of Compound (I) has a peak in a DSC thermogram at about 175.8° C. In particular embodiments, the thermal event at about 175.8° C. is a melting event. In certain embodiments, the crystalline Compound (I) melts at about 175.8° C.

In certain embodiments, the invention relates to Form A of Compound (I):

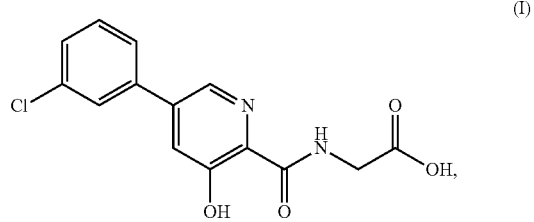 [SMILES: O=C(O)CNC(=O)c1ncc(-c2cccc(Cl)c2)cc1O]

(I)

wherein Form A of Compound (I) is at least 99.5% pure as measured by HPLC.

In certain embodiments, Form A of Compound (I) has an X-ray powder diffraction pattern comprising one, two, three, four, or five peaks at approximately 18.1, 20.3, 22.9, 24.0, and 26.3 °2θ.

In certain embodiments, Form A of Compound (I) has a peak in a DSC thermogram at 175.8° C. In particular embodiments, the thermal event at about 175.8° C. is a melting event. In certain embodiments, Form A of Compound (I) melts at about 175.8° C.

In certain embodiments, Form A of Compound (I) is at least about 99.6% pure, at least about 99.7% pure, at least about 99.8% pure, or at least about 99.9% pure. In certain embodiments, the purity may be determined e.g., by HPLC.

In certain embodiments, Form A of Compound (I) is substantially free of a compound of Formula (II):

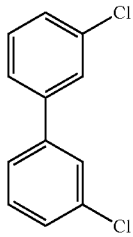

(II)

as determined by GC/MS. In certain embodiments, the crystalline compound comprises less than about 100 ppm, less than about 50 ppm, less than about 10 ppm, or less than 1 ppm of a compound of Formula (II) as determined by GC/MS. In certain embodiments, Form A of Compound (I) comprises an amount of Formula (II) that is less than a detectable amount by GC/MS.

In certain embodiments, the invention relates to Form B of Compound (I):

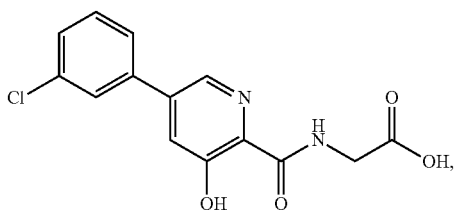

(I)

which has an X-ray powder diffraction pattern as shown in FIG. 11.

In certain embodiments, the invention relates to Form B of Compound (I):

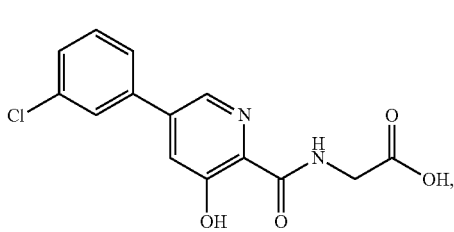

(I)

which has an X-ray powder diffraction pattern as shown in FIG. 12.

In certain embodiments, Form A, Form B and Form C of Compound (I) exist in the following zwitterionic form:

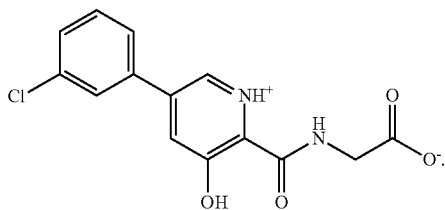

Also provided herein are pharmaceutical compositions comprising a single-component crystal form, a multiple-component crystal form, a single-component amorphous form and/or a multiple-component amorphous form of Compound (I) and a pharmaceutically acceptable diluent, excipient or carrier. In certain embodiments, the invention relates to pharmaceutical compositions comprising one or more of the solid forms described herein, such as Form A, Form B or Form C of Compound (I).

Further embodiments herein provide methods of making, isolating and/or characterizing the solid forms of the invention.

4. BRIEF DESCRIPTION OF THE FIGURES

5. DETAILED DESCRIPTION OF THE INVENTION

5.1 Definitions

Figure 1:
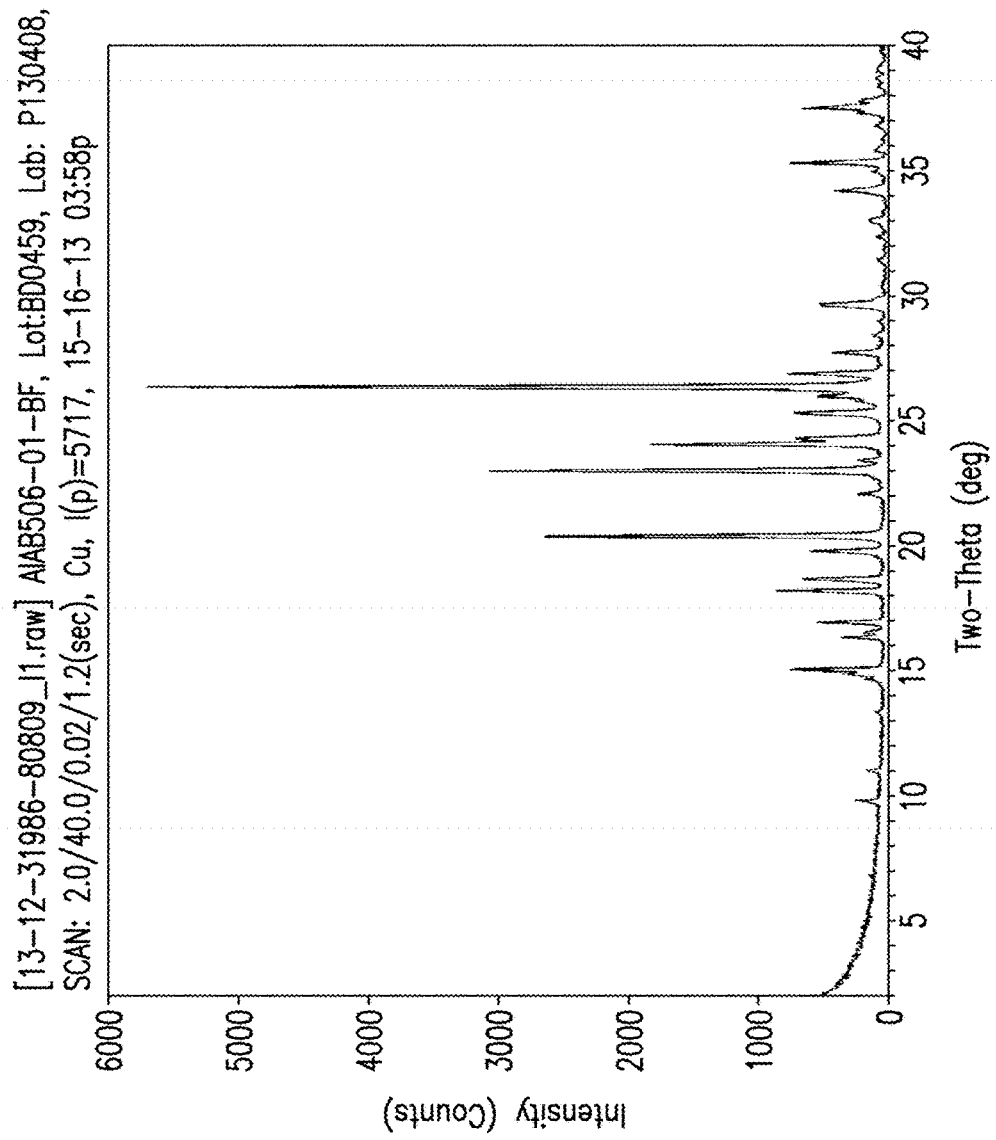
FIG. 1 shows an X-ray powder diffraction (XRPD) analysis of Compound (I), Form A.

As used herein, the term "anemia" is art-recognized and is defined by hemoglobin threshold as follows:

| Age or Gender Group | Hemoglobin Threshold (g/dL) |
| --- | --- |
| Children (0.50-4.99 yrs.) | 11.0 |
| Children (5.00-11.99 yrs.) | 11.5 |
| Children (12.00-14.99 yrs.) | 12.0 |
| Non-pregnant Women (≥15.00 yrs) | 12.0 |
| Pregnant Women | 11.0 |
| Men (≥15.00 yrs) | 13.0 |

Anemia may be chronic (e.g., anemia secondary to chronic kidney disease, anemia secondary to chronic heart failure, idiopathic anemia of aging, anemia of chronic disease, such as inflammatory bowel disease or rheumatoid arthritis, myelodysplastic syndrome, bone marrow fibrosis, and other aplastic or dysplastic anemias), subacute (e.g., chemotherapy induced anemia, such as chemotherapy for treating cancer, heptatitis C, or other chronic disease that reduces bone marrow production), acute (e.g., blood loss from injury or surgery), nutrition related (e.g., iron deficiency or vitamin B12 deficiency), or hemaglobinpathies (e.g., sickle cell disease, thalassemia, etc.).

As used herein, the term "Compound (I)" means the compound {[5-(3-chlorophenyl)-3-hydroxypyridine-2-carbonyl]amino}acetic acid Compound (I) has the following structure:

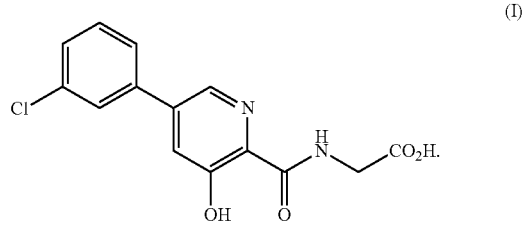 [SMILES: O=C(O)CNC(=O)c1ncc(-c2cccc(Cl)c2)cc1O]

(I)

In certain embodiments, the compound may be {[5-(3-chlorophenyl)-3-hydroxypyridine-2-carbonyl]amino}acetic acid, while in certain alternative embodiments, the compound may be a pharmaceutically acceptable salt of {[5-(3-chlorophenyl)-3-hydroxypyridine-2-carbonyl]amino}acetic acid. In certain alternative embodiments, the compound may be a solvate of {[5-(3-chlorophenyl)-3-hydroxypyridine-2-carbonyl]amino}acetic acid. In certain alternative embodiments, the compound may be a hydrate of {[5-(3-chlorophenyl)-3-hydroxypyridine-2-carbonyl]amino}acetic acid. In certain preferred embodiments, the compound can be in its parent form (i.e., not a salt, solvate, or hydrate). As used herein, Compound (I) includes any zwitterionic species as well as any pharmaceutically acceptable salts.

As used herein, the terms "prevent", "preventing" and "prevention" are art-recognized, and when used in relation to a condition, such as a local recurrence, a disease or any other medical condition, such as those described herein, is well understood in the art, and includes administration of a compound, such as Compound (I) or a pharmaceutically acceptable salt, solvate or hydrate thereof, which reduces the frequency of, or delays the onset of, symptoms of a medical condition in a subject relative to a subject which does not receive the composition.

As used herein, the terms "treat", "treating" and "treatment" refer to the reversing, reducing, or arresting the symptoms, clinical signs, and underlying pathology of a disease condition, such as those described herein, in manner to improve or stabilize a subject's condition. The terms "treat" and "treatment" also refer to the eradication or amelioration of the disease or symptoms associated with the disease. In certain embodiments, such terms refer to minimizing the spread or worsening of the disease resulting from the administration of Compound (I) or a pharmaceutically acceptable salt, solvate or hydrate thereof to a patient with such a disease.

As used herein, the term "pharmaceutically acceptable salt" refers to a salt prepared from pharmaceutically acceptable non-toxic acids or bases including inorganic acids and bases and organic acids and bases. Suitable pharmaceutically acceptable base addition salts for Compound (I) include, but are not limited to, lithium, calcium, magnesium, zinc, bismuth, ammonium (including alkyl substituted ammonium), meglumine and choline. Suitable non-toxic acids include, but are not limited to, inorganic and organic acids such as acetic, alginic, anthranilic, benzenesulfonic, benzoic, camphorsulfonic, citric, ethanesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Other examples of salts are well known in the art. See, e.g., Remington's Pharmaceutical Sciences, 22nd ed., Pharmaceutical Press, (2012).

As used herein, the term "hydrate" means 5-(3-chlorophenyl)-3-hydroxypyridine-2-carbonyl]amino}acetic acid or a pharmaceutically acceptable salt thereof, that further includes a stoichiometric or non-stoichiometric amount of water bound by non-covalent intermolecular forces.

As used herein, the term "solvate" means 5-(3-chlorophenyl)-3-hydroxypyridine-2-carbonyl]amino}acetic acid or a pharmaceutically acceptable salt thereof, that further includes a stoichiometric or non-stoichiometric amount of a solvent, other than water, bound by non-covalent intermolecular forces.

As used herein, the term "HIF prolyl hydroxylase" is art-recognized and may be abbreviated as "PHD". HIF prolyl hydroxylase is also known as "prolyl hydroxylase domain-containing protein" which may be abbreviated as "PHD". In this regard, there are three different PHD isoforms, PHD1, PHD2, and PHD3, also referred to as EGLN2, EGLN1, and EGLN3, or HPH3, HPH2, and HPH1, respectively.

The terms "solid form," "solid forms" and related terms, when used herein to refer to Compound (I), refer to a physical form comprising Compound (I) which is not predominantly in a liquid or a gaseous state. Crystal forms and amorphous forms are examples of solid forms. In one embodiment, the solid form is Form A. In another embodiment, the solid form is Form B. In another embodiment, the solid form is Form C.

The term "crystalline" and related terms used herein, when used to describe a substance, component, product, or form, means that the substance, component or product is substantially crystalline as determined by X-ray diffraction. See, e.g., Remington's Pharmaceutical Sciences, 22nd ed., Pharmaceutical Press, (2012).; *The United States Pharmacopoeia*, 30th ed., (2011).

The term "crystal form," "crystalline form" and related terms herein refer to a crystalline solid form comprising a chemical compound, and may refer to a particular single-component or multiple-component crystal form, including, but not limited to, a polymorph, a solvate, a hydrate or other molecular complex, a salt, a solvate of a salt, a hydrate of a salt, or other molecular complex of a salt, or a polymorph thereof.

The terms "polymorphs," "polymorphic forms" and related terms herein refer to two or more crystal forms that comprise the same molecule, molecules or ions. Different polymorphs may have different physical properties such as, for example, melting temperatures, heats of fusion, solubilities, dissolution rates and/or vibrational spectra as a result of the arrangement or conformation of the molecules or ions in the crystal lattice. The differences in physical properties exhibited by polymorphs affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing; for example, one polymorph might be more likely to form solvates or might be difficult to filter and wash free of impurities (e.g., particle shape and size distribution might be different between polymorphs).

Techniques for characterizing crystal forms and amorphous forms include, but are not limited to, thermal gravimetric analysis (TGA), melting point, differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy (e.g., polaraized light microscopy), hot stage optical microscopy, scanning electron microscopy (SEM), electron crystallography, dynamic vapor sorption (DVS), and quantitative analysis, particle size analysis (PSA), surface area analysis, solubility studies and dissolution studies.

The term "amorphous," "amorphous form," and related terms used herein mean that the substance, component or product in question is not substantially crystalline as determined by X-ray diffraction. In certain embodiments, a sample comprising an amorphous form of a substance may be substantially free of other amorphous forms and/or crystal forms.

As used herein, and unless otherwise specified, the terms "about" and "approximately," when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately," when used in this context, contemplate a dose, amount, or weight percent within 15%, more specifically within 10%, more specifically within 5%, of the specified dose, amount, or weight percent.

As used herein, and unless otherwise specified, the terms "about" and "approximately," when used in connection with a numeric value or range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. Specifically, the terms "about" and "approximately," when used in this context, indicate that the numeric value or range of values may vary, in particular embodiments, within 20%, 10%, 9%, 8%, 7%, 6%, 5%, 4%, 3%, 2%, 1.5%, 1%, 0.5%, or 0.25% of the recited value or range of values. With respect to XRPD, values given are ±0.2 degrees 2 theta.

As used herein, an "effective amount" refers to that amount of Compound (I) or a pharmaceutically acceptable salt, solvate or hydrate thereof sufficient to provide a therapeutic benefit in the treatment of the disease or to delay or minimize symptoms associated with the disease, such as any disease or condition described herein.

The terms "subject" and "patient," unless otherwise specified, are defined herein to include animals such as mammals, including, but not limited to, primates (e.g., humans), cows, sheep, goats, horses, dogs, cats, rabbits, rats, mice and the like. In specific embodiments, the subject or patient is a human. In certain embodiments, the patient has a disease or condition as described herein.

5.2 Solid Forms

Certain embodiments herein provide single-component and multiple-component (e.g., salts, solvates, hydrates) solid forms comprising Compound (I), which has the chemical structure shown below:

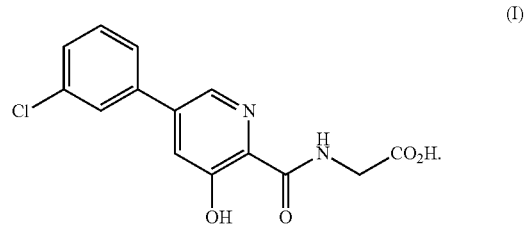 [SMILES: O=C(O)CNC(=O)c1ncc(-c2cccc(Cl)c2)cc1O]

(I)

Compound (I) may be synthesized or obtained according to any method apparent to those of skill in the art based upon the teachings herein, including the methods described in detail in the examples below. Compound (I) may also be prepared according to the methods described in U.S. Pat. No. 7,811,595, filed Jun. 26, 2007 (See inter alia Schemes I and II and accompanying synthetic procedures in columns 15-17, and 25) and U.S. Publication 2012-0309977 (U.S. patent application Ser. No. 13/488,554), filed in Jun. 5, 2012 (See inter alia paragraphs [0254]-[267]), the entireties of each of which is incorporated by reference herein. Solid forms of Compound (I) may then be prepared from the Compound (I) made by such methods.

Certain embodiments herein provide single-component solid forms of the free acid of Compound (I) having utility for the treatment or prevention of anemia (e.g., anemia secondary to or associated with chronic kidney disease, anemia secondary to chronic heart disease, idiopathic anemia of aging, anemia of chronic disease, myelodysplastic syndrome, bone marrow fibrosis, other aplastic or dysplastic anemias, chemotherapy induced anemia (including chemotherapy for treating cancer, hepatitis C, or other chronic drug therapy that reduces bone marrow production), anemia resulting from blood loss, anemia resulting from iron deficiency, anemia resulting from vitamin B12 deficiency, sickle cell disease, or thalassemia). Accordingly, provided herein are methods for the treatment of anemia, comprising administering to a patient having anemia an effective amount of a solid form of Compound (I).

The single-component solid forms of Compound (I) can be prepared by any method apparent to those skilled in the art based upon the teachings herein. The single-component solid forms of Compound (I) can also be prepared according to the techniques described herein, including the methods described in detail in the examples below.

5.2.1 Form A of Compound (I)

Certain embodiments herein provide the Form A crystal form of Compound (I). In certain embodiments, Form A of Compound (I) can be obtained from a Compound (I) as prepared in a procedure according to e.g., U.S. Pat. No. 7,811,595, filed Jun. 26, 2007 (See inter alia Schemes I and II and accompanying synthetic procedures in columns 15-17, and 25) and U.S. Publication 2012-0309977 (U.S. patent application Ser. No. 13/488,554), filed in Jun. 5, 2012 (See inter alia paragraphs [0254]-[267]) followed by subjecting the resulting Compound (I) to a crystallization procedure as described herein below.

A representative XRPD pattern of Form A of Compound (I) is provided in FIG. 1. In certain embodiments, Form A of Compound (I) is characterized by XRPD peaks located at one or more of the following approximate positions: 9.8, 11.0, 13.3, 14.6, 14.8, 15.0, 16.3, 16.4, 16.9, 18.1, 18.6, 19.7, 20.3, 22.0, 22.9, 23.3, 24.0, 24.2, 25.2, 25.7, 25.9, 26.3, 26.8, 27.6, 28.3, 28.9, 29.6, 29.8, 30.3, 31.3, 32.2, 32.9, 34.1, 34.9, 35.2, 35.7, 36.2, 36.7, 37.2, 37.4, 37.7, 38.3, 38.6, and 38.9 degrees 2θ. In particular embodiments, Form A of Compound (I) is characterized by XRPD peaks located at one, two, three, four, five or six, seven, eight, nine, ten, eleven, twelve, or thirteen of the following approximate positions: 15.0, 18.1, 18.6, 19.7, 20.3, 22.9, 24.0, 24.2, 25.2, 26.3, 26.8, 35.2, and 37.4 degrees 2θ. In certain embodiments, Form A of Compound (I) has an XRPD pattern comprising peaks at approximately 18.1, 20.3, 22.9, 24.0, 26.3, 26.8, and 35.2 degrees °2θ. In certain embodiments, Form A of Compound (I) has an XRPD pattern further comprising peaks at approximately 18.1, 20.3, 22.9, 24.0, and 26.3 degrees °2θ.

Figure 3:
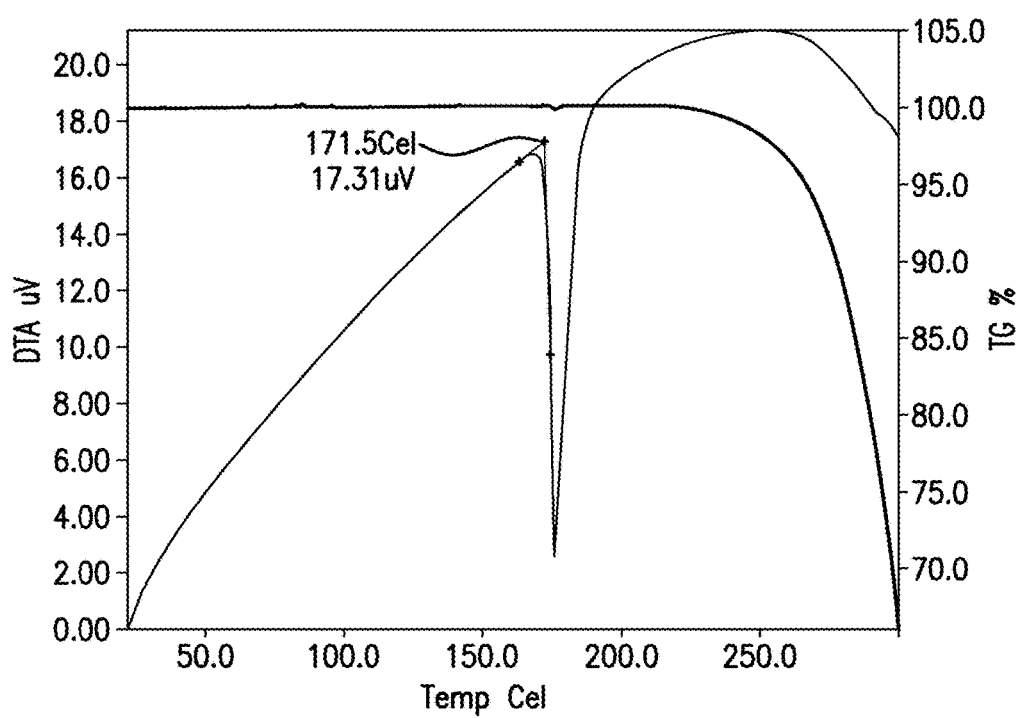
FIG. 3 shows a thermal gravimetric/differential thermal analysis (TG/DTA or TGA) analysis of Compound (I), Form A.
Figure 4:
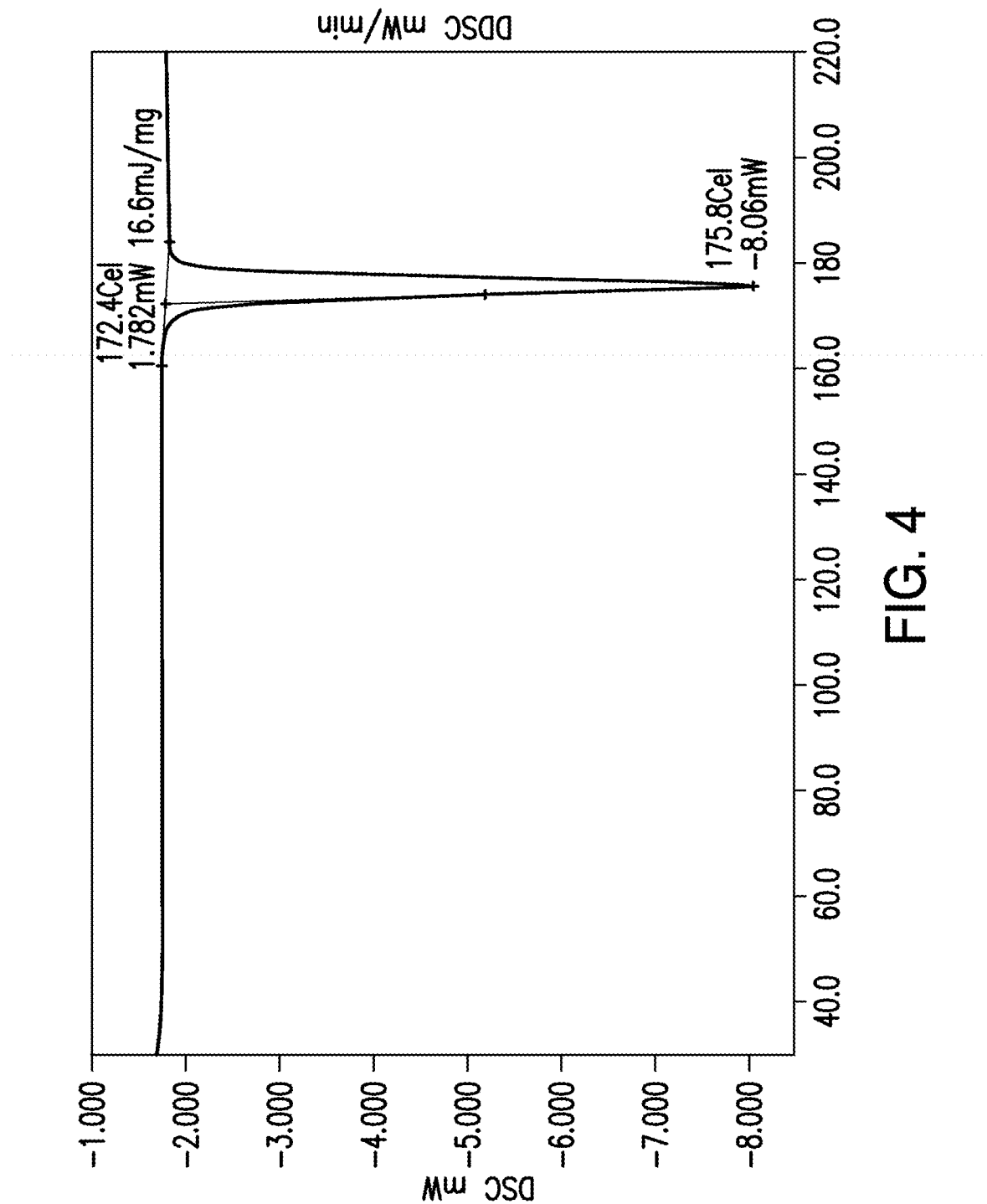
FIG. 4 shows a differential scanning calorimetry (DSC) analysis of Compound (I), Form A.

Representative thermal characteristics of Form A of Compound (I) are shown in FIG. 3 and FIG. 4. A representative TGA/DTA thermogram, presented in FIG. 3, exhibits negligible weight loss from ambient, then significant weight loss above ca. 220° C. which is consistent with decomposition. The DTA shows a single sharp endotherm with an onset of 171.5° C.

A representative DSC thermogram, presented in FIG. 4, exhibits shows a single sharp endotherm with an onset at about 172.4° C. and a peak at about 175.8° C. In certain embodiments, the thermal event at about 175.8° C. is a melting event. In certain embodiments, Form A melts at about 175.8° C. In certain embodiments, Form A is unsolvated. In certain embodiments, Form A is anhydrous.

Form A of Compound (I) exhibits desirable characteristics for the synthesis, processing and manufacture of drug product containing Compound (I). For example, in certain embodiments, Form A of Compound (I) has an advantageous stability profile, which is an important characteristic for processing and manufacturing.

In certain embodiments, Form A of Compound (I) is non-hygroscopic, e.g., water sorption at 90% relative humidity (RH) is less than about 0.5%. For example, in certain embodiments, when subjected to moisture sorption analysis, Form A exhibits a mass gain of less than about 0.4%, less than about 0.3%, less than about 0.2%, when increased from about 0% to about 90% RH. In certain embodiments, Form A exhibits a mass gain of about 0.13% when increased from about 0% to about 90% RH. In certain embodiments, following moisture sorption analysis, the XRPD pattern of the Form A material is substantially unchanged. A representative dynamic vapor sorption (DVS) isotherm plot of Compound (I), Form A is presented in FIG. 5. In certain embodiments, the moisture sorption analysis may be determined using a ramping profile from 20-90-20% relative humidity (RH) in 10% increments, maintaining the sample at each step until a stable weight had been achieved (99.5% step completion) or 1000 minutes have elapsed. After completion of the sorption cycle, the sample may be dried using the same procedure, but all the way down to about 0% RH and finally taken back to the starting point of 20% RH.

In certain embodiments, Form A of Compound (I) comprises small particles with the majority of the particles being less than 100 μm. In certain embodiment, Form A of Compound (I) comprises particles with an average size of less than 100 μm. A representative particle size analysis is presented in FIG. 7.

In certain embodiments, Form A of Compound (I) is substantially pure. In certain embodiments Form A of Compound (I) is at least about 99.6% pure, at least about 99.7% pure, at least about 99.8% pure, or at least about 99.9% pure. In certain embodiments, the purity may be determined e.g., by HPLC.

In certain embodiments Form A of Compound (I) is substantially free of a compound of Formula (II):

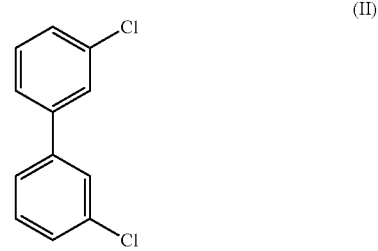 [SMILES: Clc1cccc(-c2cccc(Cl)c2)c1]

(II)

as determined by GC/MS In certain embodiments, the crystalline compound comprises less than about 100 ppm, less than about 75 ppm, less than about 50 ppm, less than about 25 ppm, less than about 10 ppm, less than about 5 ppm, less than about 3 ppm, less than about 2 ppm, or less than about 1 ppm of a compound of Formula (II) as determined by GC/MS. In certain embodiments, Form A of Compound (I) comprises an amount of Formula (II) that is less than a detectable amount by GC/MS.

In certain embodiments, Form A of Compound (I) comprises less than about 15%, less than about 10% or less than about 5% by weight of amorphous Compound (I).

In certain embodiments, Form A of Compound (I) comprises less than 15%, less than 10%, or less than 5% by weight of any other crystalline Compound (I).

5.2.2 Form B of Compound (I)

Certain embodiments herein provide the Form B crystal form of Compound (I). In certain embodiments, Form B of Compound (I) can be obtained from a Compound (I) as prepared in a procedure according to e.g., U.S. Pat. No. 7,811,595, filed Jun. 26, 2007 (See inter alia Schemes I and II and accompanying synthetic procedures in columns 15-17, and 25) and U.S. Publication 2012-0309977 (U.S. patent application Ser. No. 13/488,554), filed in Jun. 5, 2012 (See inter alia paragraphs [0254]-[267]) followed by subjecting the resulting Compound (I) to a crystallization procedure as described herein below.

Figure 11:
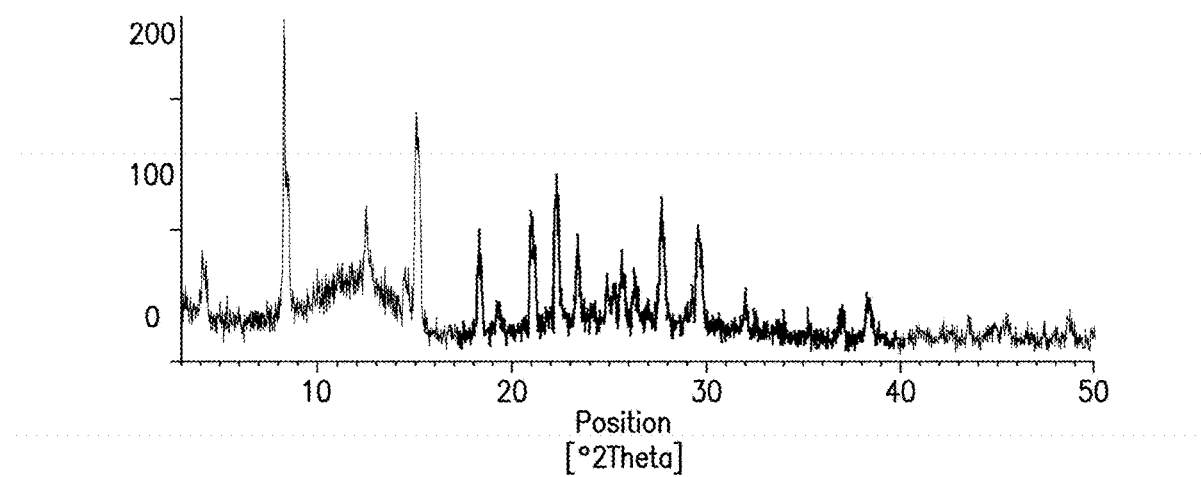
FIG. 11 shows an X-ray powder diffraction (XRPD) analysis of Compound (I), Form B.

A representative XRPD pattern of Form B of Compound (I) is provided in FIG. 11. In certain embodiments, Form B of Compound (I) is characterized by XRPD peaks located at one or more of the following approximate positions: 8.6, 15.3, 18.6, 21.3, 22.7, 23.8, 28.1 and 30.0 degrees 2θ. In particular embodiments, Form B of Compound (I) is characterized by XRPD peaks located at one, two, three or four of the following approximate positions: 8.6, 15.3, 22.7 and 28.1 degrees 2θ.

In certain embodiments, Form B of Compound (I) is substantially pure. In certain embodiments Form B of Compound (I) is at least about 99.6% pure, at least about 99.7% pure, at least about 99.8% pure, or at least about 99.9% pure. In certain embodiments, the purity may be determined e.g., by HPLC.

In certain embodiments Form B of Compound (I) is substantially free of a compound of Formula (II):

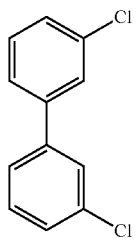

(II)

as determined by GC/MS In certain embodiments, the crystalline compound comprises less than about 100 ppm, less than about 75 ppm, less than about 50 ppm, less than about 25 ppm, less than about 10 ppm, less than about 5 ppm, less than about 3 ppm, less than about 2 ppm, or less than about 1 ppm of a compound of Formula (II) as determined by GC/MS. In certain embodiments, Form B of Compound (I) comprises an amount of Formula (II) that is less than a detectable amount by GC/MS.

In certain embodiments, Form B of Compound (I) comprises less than about 15%, less than about 10% or less than about 5% by weight of amorphous Compound (I).

In certain embodiments, Form B of Compound (I) comprises less than 15%, less than 10%, or less than 5% by weight of any other crystalline Compound (I).

5.2.3 Form C of Compound (I)

Certain embodiments herein provide the Form C crystal form of Compound (I). In certain embodiments, Form C of Compound (I) can be obtained from a Compound (I) as prepared in a procedure according to e.g., U.S. Pat. No. 7,811,595, filed Jun. 26, 2007 (See inter alia Schemes I and II and accompanying synthetic procedures in columns 15-17, and 25) and U.S. Publication 2012-0309977 (U.S. patent application Ser. No. 13/488,554), filed in Jun. 5, 2012 (See inter alia paragraphs [0254]-[267]) followed by subjecting the resulting Compound (I) to a crystallization procedure as described herein below.

Figure 12:
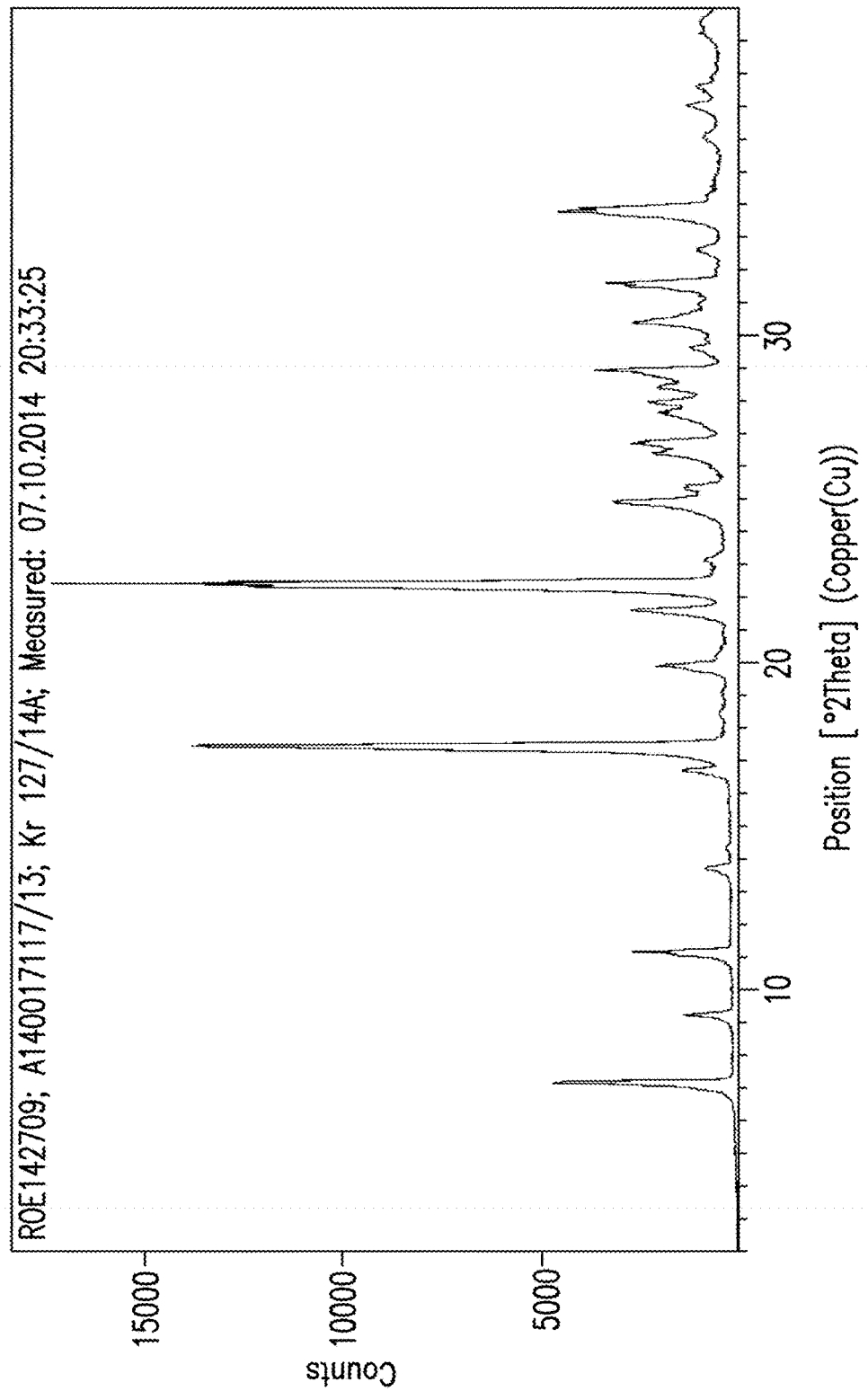
FIG. 12 shows an X-ray powder diffraction (XRPD) analysis of Compound (I), Form C.

A representative XRPD pattern of Form C of Compound (I) is provided in FIG. 12. In certain embodiments, Form C of Compound (I) is characterized by XRPD peaks located at one or more of the following approximate positions: 7.2, 9.2, 11.1, 13.7, 14.3, 16.7, 17.4, 18.4, 19.1, 19.9, 20.1, 21.6, 22.3, 22.4, 22.4, 23.1, 24.8, 25.3, 26.3, 26.6, 27.6, 27.9, 28.3, 28.9, 29.5, 30.3, 31.4, 31.5, 32.5, 33.7, 33.8, 36.0, 37.0, 37.5, 39.1 and 39.5 degrees 2θ. In particular embodiments, Form C of Compound (I) is characterized by XRPD peaks located at one, two, three, four, five or six, seven or eight of the following approximate positions: 7.2, 17.4, 22.3, 22.4, 22.4, 28.9, 33.7 and 33.8 degrees 2θ. In certain embodiments, Form C of Compound (I) has an XRPD pattern comprising peaks at approximately 17.4, 22.3 and 22.4 degrees °2θ. In certain embodiments, Form C of Compound (I) has an XRPD pattern further comprising an additional peak at approximately 22.4 degrees °2θ. In certain embodiments, Form C of Compound (I) has an XRPD pattern further comprising peaks at approximately 7.2, 28.9, 33.7 and 33.8 degrees °2θ.

In certain embodiments, Form C of Compound (I) is substantially pure. In certain embodiments Form C of Compound (I) is at least about 99.6% pure, at least about 99.7% pure, at least about 99.8% pure, or at least about 99.9% pure. In certain embodiments, the purity may be determined e.g., by HPLC.

In certain embodiments Form C of Compound (I) is substantially free of a compound of Formula (II):

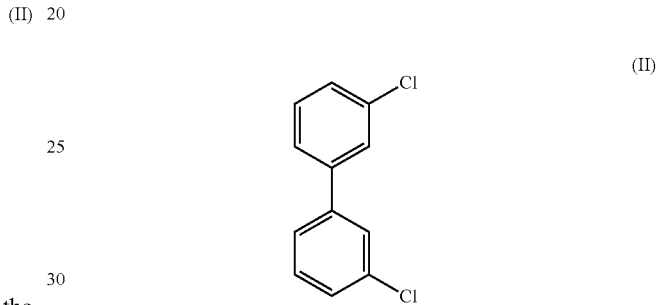

(II)

as determined by GC/MS In certain embodiments, the crystalline compound comprises less than about 100 ppm, less than about 75 ppm, less than about 50 ppm, less than about 25 ppm, less than about 10 ppm, less than about 5 ppm, less than about 3 ppm, less than about 2 ppm, or less than about 1 ppm of a compound of Formula (II) as determined by GC/MS. In certain embodiments, Form C of Compound (I) comprises an amount of Formula (II) that is less than a detectable amount by GC/MS.

In certain embodiments, Form C of Compound (I) comprises less than about 15%, less than about 10% or less than about 5% by weight of amorphous Compound (I).

In certain embodiments, Form C of Compound (I) comprises less than 15%, less than 10%, or less than 5% by weight of any other crystalline Compound (I).

5.3 Methods of Making

Certain embodiments herein provide a crystalline Compound (I), such as Form A. In certain embodiments, Form A of Compound (I) may be obtained from Compound (I) as prepared according to e.g., U.S. Pat. No. 7,811,595 and/or U.S. patent application Ser. No. 13/488,554 and then subjecting the resulting Compound (I)

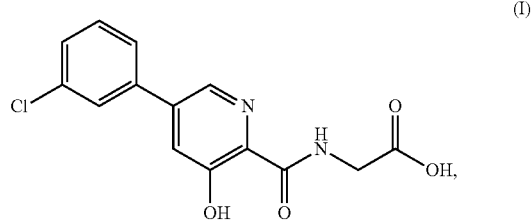 [SMILES: O=C(O)CNC(=O)c1ncc(-c2cccc(Cl)c2)cc1O]

(I)

to a procedure comprising a) preparing a solution of Compound (I) in an organic solvent;

b) bringing the solution to super-saturation to cause formation of crystals; and c) isolating the crystals;

wherein the crystalline Compound (I), such as Form A of Compound (I) is substantially free of any other crystalline compound of Formula (I), such as where the crystalline Compound (I), such as Form A of Compound (I) comprises less than about 15%, less than about 10%, less than about 5%, or less than 1% by weight of any other crystalline Compound (I).; or wherein the crystalline Compound (I), such as Form A of Compound (I) is substantially free of a compound of Formula (II):

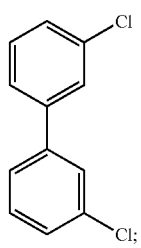

(II)

as determined by GC/MS, such as where the crystalline Compound (I), such as Form A of Compound (I) comprises less than about 100 ppm, less than about 75 ppm, less than about 50 ppm, less than about 25 ppm, less than about 10 ppm, less than about 5 ppm, less than about 3 ppm, less than about 2 ppm, or less than about 1 ppm of a compound of Formula (II) as determined by GC/MS; or wherein the crystalline Compound (I), such as Form A of Compound (I) is substantially free of amorphous Compound (I), such as where the crystalline compound (I) comprises less than about 15%, less than about 10%, less than about 5%, or less than 1% by weight of amorphous Compound (I).

In certain such embodiments, the crystalline Compound (I) is at least 99.5% pure as measured by HPLC.

In certain such embodiments, the organic solvent is selected from acetone, methyl isobutyl ketone, n-heptane, tetrahydrofuran, methyl tethydrofuran (e.g., 2-methyl tetrahydrofuran) and water, or any combination thereof. In certain such embodiments, the organic solvent is acetone.

In certain such embodiments, the process further comprises filtering the solution through a charcoal filter. In certain embodiments, such filtering may be performed after preparing the solution of Compound (I) in an organic solvent. In certain embodiments, such filtering may be performed prior to bringing the solution to super-saturation.

In certain embodiments, bringing the solution to super-saturation comprises addition of an anti-solvent, allowing the solution to cool, reducing the volume of the solution, solvent exchange, or any combination thereof. In certain such embodiments where bringing the solution to super-saturation comprises reducing the volume of the solution, the volume reduction is performed by evaporation. In certain such embodiments where bringing the solution to super-saturation comprises the addition of anti-solvent, the anti-solvent is water or heptane-2-propanol. In certain such embodiments, bringing the solution to super-saturation comprises allowing the solution to cool and addition of anti-solvent. In certain alternative such embodiments, bringing the solution to super-saturation comprises solvent exchange and allowing the solution to cool.

In certain embodiments where bringing the solution to super-saturation comprises solvent exchange, the solvent exchange comprises a distillative solvent exchange under reduced pressure. In certain such embodiments, acetone is exchanged for methyl isobutyl ketone.

In certain embodiments where bringing the solution to super-saturation comprises allowing the solution to cool, the solution is allowed to cool to between about 19° C. and about 25° C., or even to between about 0° C. and about 5° C.

In certain embodiments, the method further comprises seeding the solution with a crystalline Compound (I), such as Form A of Compound (I).

In certain embodiments, the method further comprises washing the crystals. In certain such embodiments, the washing comprises washing the crystals with a liquid selected from acetone, methyl isobutyl ketone, n-heptane, and water, or any combination thereof. In certain such embodiments, the washing comprises washing with a combination of acetone and water. In certain alternative such embodiments, the washing comprises washing with methyl isobutyl ketone.

In certain embodiments, isolating the crystals comprises filtering the crystals. In certain embodiments, the method further comprises drying the isolated crystals under reduced pressure, optionally at an elevated temperature. In certain such embodiments, the drying is performed at a temperature of about 50° C.

In certain embodiments, the invention relates to a crystalline Compound (I), such as Form A of Compound (I), which is produced by a process comprising:

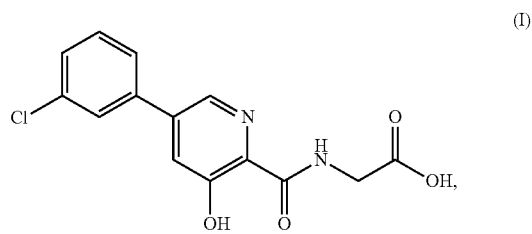 [SMILES: O=C(O)CNC(=O)c1ncc(-c2cccc(Cl)c2)cc1O]

(I)

a) preparing a solution of Compound (I) in an organic solvent;

b) bringing the solution to super-saturation to cause formation of crystals; and c) isolating the crystals; with optional drying of the crystals.

the crystalline Compound (I), such as Form A of Compound (I) is substantially free of any other crystalline Compound (I); or wherein the crystalline Compound (I), such as Form A of Compound (I) is substantially free of a compound of Formula (II):

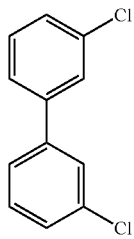

(II)

as determined by GC/MS; or
wherein the crystalline Compound (I), such as Form A of Compound (I) is substantially free of amorphous Compound (I).

In certain such embodiments, the crystalline Compound (I) is at least 99.5% pure as measured by HPLC.

In certain such embodiments, the organic solvent is selected from acetone, methyl isobutyl ketone, n-heptane, and water, or any combination thereof. In certain such embodiments, the organic solvent is acetone.

In certain such embodiments, the process further comprises filtering the solution through a charcoal filter. In certain embodiments, such filtering may be performed after preparing the solution of Compound (I) in an organic solvent. In certain embodiments, such filtering may be performed prior to bringing the solution to super-saturation.

In certain embodiments, bringing the solution to super-saturation comprises addition of an anti-solvent, allowing the solution to cool, reducing the volume of the solution, solvent exchange, or any combination thereof. In certain such embodiments where bringing the solution to super-saturation comprises reducing the volume of the solution, the volume reduction is performed by evaporation. In certain such embodiments where bringing the solution to super-saturation comprises the addition of anti-solvent, the anti-solvent is water. In certain such embodiments, bringing the solution to super-saturation comprises allowing the solution to cool and addition of anti-solvent. In certain alternative such embodiments, bringing the solution to super-saturation comprises solvent exchange and allowing the solution to cool.

In certain embodiments where bringing the solution to super-saturation comprises solvent exchange, the solvent exchange comprises a distillative solvent exchange under reduced pressure. In certain such embodiments, acetone is exchanged for methyl isobutyl ketone.

In certain embodiments where bringing the solution to super-saturation comprises allowing the solution to cool, the solution is allowed to cool to between about 19° C. and about 25° C., or even to between about 0° C. and about 5° C.

In certain embodiments, the process further comprises seeding the solution with a crystalling Compound (I), such as Form A of Compound (I).

In certain embodiments, the process further comprises washing the crystals. In certain such embodiments, the washing comprises washing the crystals with a liquid selected from acetone, methyl isobutyl ketone, n-heptane, and water, or any combination thereof. In certain such embodiments, the washing comprises washing with a combination of acetone and water. In certain alternative such embodiments, the washing comprises washing with methyl isobutyl ketone.

In certain embodiments, isolating the crystals comprises filtering the crystals. In certain embodiments, the process further comprises drying the isolated crystals under reduced pressure, optionally at an elevated temperature. In certain such embodiments, the drying is performed at a temperature of about 50° C.

In certain embodiments, Form B of Compound (I) may be obtained from Compound (I) as prepared according to e.g., U.S. Pat. No. 7,811,595 and/or U.S. patent application Ser. No. 13/488,554 and then subjecting the resulting Compound (I)

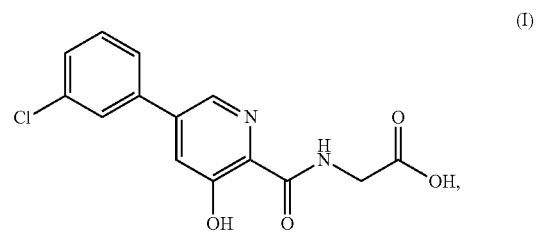 [SMILES: O=C(O)CNC(=O)c1ncc(-c2cccc(Cl)c2)cc1O]

(I)

to a procedure comprising
a) preparing a solution of Compound (I) in acetonitrile; and
b) evaporating the solvent.

In certain embodiments, the crystalline Compound (I), such as Form B of Compound (I) is substantially free of any other crystalline compound of Formula (I), such as where the cystalline Compound (I), such as Form B of Compound (I) comprises less than about 15%, less than about 10%, less than about 5%, or less than 1% by weight of any other crystalline Compound (I).; or
wherein the crystalline Compound (I), such as Form B of Compound (I) is substantially free of a compound of Formula (II):

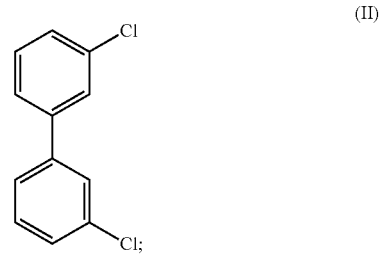 [SMILES: Clc1cccc(-c2cccc(Cl)c2)c1]

(II)

as determined by GC/MS, such as where the crystalline Compound (I), such as Form B of Compound (I) comprises less than about 100 ppm, less than about 75 ppm, less than about 50 ppm, less than about 25 ppm, less than about 10 ppm, less than about 5 ppm, less than about 3 ppm, less than about 2 ppm, or less than about 1 ppm of a compound of Formula (II) as determined by GC/MS; or
wherein the crystalline Compound (I), such as Form B of Compound (I) is substantially free of amorphous Compound (I), such as where the crystalline compound (I) comprises less than about 15%, less than about 10%, less than about 5%, or less than 1% by weight of amorphous Compound (I).

In certain such embodiments, the crystalline Compound (I), such as Form B of Compound (I) is at least 99.5% pure as measured by HPLC.

In certain embodiments, Form C of Compound (I) may be obtained from Compound (I) as prepared according to e.g., U.S. Pat. No. 7,811,595 and/or U.S. patent application Ser. No. 13/488,554 and then subjecting the resulting Compound (I)

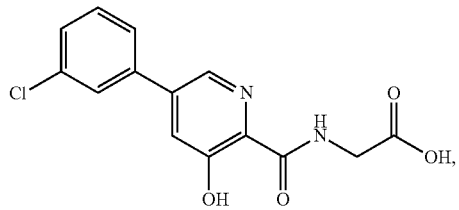

(I)

to a procedure comprising
a) preparing a solution of Compound (I) in 2-methyltetrahydrofuran;
b) adding n-heptane;
c) heating the suspension (e.g., to about 40-50° C.);
d) cooling the suspension (e.g., to about 0-10° C.); and
c) isolating the crystals.

In certain embodiments, the crystalline Compound (I), such as Form C of Compound (I) is substantially free of any other crystalline compound of Formula (I), such as where the cystalline Compound (I), such as Form C of Compound (I) comprises less than about 15%, less than about 10%, less than about 5%, or less than 1% by weight of any other crystalline Compound (I).; or
wherein the crystalline Compound (I), such as Form C of Compound (I) is substantially free of a compound of Formula (II):

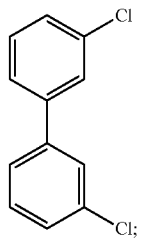

(II)

as determined by GC/MS, such as where the crystalline Compound (I), such as Form C of Compound (I) comprises less than about 100 ppm, less than about 75 ppm, less than about 50 ppm, less than about 25 ppm, less than about 10 ppm, less than about 5 ppm, less than about 3 ppm, less than about 2 ppm, or less than about 1 ppm of a compound of Formula (II) as determined by GC/MS; or
wherein the crystalline Compound (I), such as Form C of Compound (I) is substantially free of amorphous Compound (I), such as where the crystalline compound (I) comprises less than about 15%, less than about 10%, less than about 5%, or less than 1% by weight of amorphous Compound (I).

In certain such embodiments, the crystalline Compound (I), such as Form C of Compound (I) is at least 99.5% pure as measured by HPLC.

In certain embodiments, the addition of n-heptane is carried over not less than 30 minutes (e.g., about 30 to about 60 minutes). In certain embodiments, the addition of n-heptane is carried out at about 40-50° C. In certain embodiments, the suspension is heated to about 40-50° C. with stirring for at least about 1 hour (e.g., about 1 to about 2 hours). In certain embodiments, the suspension cooled to about 0-10° C. is stirred for at least about 1 hour (e.g., about 1 to about 2 hours). In certain embodiments, isolating the crystals comprises filtering the crystals. In certain embodiments, the filtered crystals are washed with cold n-heptane/2-methyltetrahydrofuran (e.g., 6:1) and dried. In certain such embodiments, the drying is performed at a temperature of not more than about 50° C. (e.g., about 50° C.) under vacuum.

5.4 Methods of Use

In certain embodiments, the invention relates to methods for treating or preventing a disease or disorder ameliorated by modulation of HIF prolyl hydroxylase (e.g., PHD1, PHD2, and/or PHD3) comprising administering to a patient having a disease ameliorated by modulation of HIF prolyl hydroxylase an effective amount of a solid form of Compound (I), such as Form A, Form B or Form C of Compound (I) or any other solid form described herein.

In certain embodiments, the invention encompasses methods of treating or preventing a disease or disorder ameliorated by inhibiting HIF prolyl hydroxylase (e.g., PHD1, PHD2, and/or PHD3), comprising administering to a patient having a disease or disorder ameliorated by inhibiting HIF prolyl hydroxylase an effective amount of a solid form of Compound (I). In certain such embodiments, the invention relates to methods of treating or preventing a disease or disorder ameliorated by inhibiting PHD1, comprising administering to a patient having a disease or disorder ameliorated by inhibiting PHD1 an effective amount of a solid form of Compound (I). In certain such embodiments, the invention relates to methods of treating or preventing a disease or disorder ameliorated by inhibiting PHD2, comprising administering to a patient having a disease or disorder ameliorated by inhibiting PHD2 an effective amount of a solid form of Compound (I). In certain such embodiments, the invention relates to methods of treating or preventing a disease or disorder ameliorated by inhibiting PHD3, comprising administering to a patient having a disease or disorder ameliorated by inhibiting PHD3 an effective amount of a solid form of Compound (I).

In certain embodiments, the invention encompasses methods of treating or preventing a disease or disorder ameliorated by stabilizing HIFα (e.g., HIF-1α, HIF-2α, and/or HIF-3α), comprising administering to a patient having a disease or disorder ameliorated by stabilizing HIFα an effective amount of a solid form of Compound (I). In certain such embodiments, the invention relates to treating or preventing a disease or disorder ameliorated by stabilizing HIF-1α, comprising administering to a patient having a disease or disorder ameliorated by stabilizing HIF-1α an effective amount of a solid form of Compound (I). In certain such embodiments, the invention relates to treating or preventing a disease or disorder ameliorated by stabilizing HIF-2α, comprising administering to a patient having a disease or disorder ameliorated by inhibiting HIF-2α an effective amount of a solid form of Compound (I). In certain such embodiments, the invention relates to treating or preventing a disease or disorder ameliorated by stabilizing HIF-3α, comprising administering to a patient having a disease or disorder ameliorated by stabilizing HIF-3α an effective amount of a solid form of Compound (I).

In certain embodiments, the invention relates to methods of treating or preventing a disease or condition related to diminished endogenous production of erythropoietin (EPO), comprising administering to a patient having a disease or disorder related to diminished endogenous production of EPO an effective amount of a solid form of Compound (I).

In certain embodiments, the invention relates to methods of treating or preventing anemia (e.g., anemia secondary to or associated with chronic kidney disease, anemia secondary to chronic heart disease, idiopathic anemia of aging, anemia of chronic disease, myelodysplastic syndrome, bone marrow fibrosis, other aplastic or dysplastic anemias, chemotherapy induced anemia (including chemotherapy for treating cancer, hepatitis C, or other chronic drug therapy that reduces bone marrow production), anemia resulting from blood loss, anemia resulting from iron deficiency, anemia resulting from vitamin B12 deficiency, sickle cell disease, or thalassemia), comprising administering to a patient having anemia an effective amount of a solid form of Compound (I). In certain embodiments, the invention relates to methods of treating anemia, such as anemia secondary to chronic kidney disease, comprising administering to a patient having anemia an effective amount of a solid form of Compound (I).

In certain embodiments, the invention relates to treating or preventing anemia secondary to chronic kidney disease (CKD), comprising administering to a patient having anemia secondary to CKD an effective amount of a solid form of Compound (I). In certain embodiments, the CKD is stage 1, 2, 3, 4, or 5 chronic kidney disease. In certain such embodiments, the CKD is stage 3, 4, or 5 chronic kidney disease. In certain embodiments, the CKD is stage 1 chronic kidney disease. In certain embodiments, the CKD is stage 2 chronic kidney disease. In certain embodiments, the CKD is stage 3 chronic kidney disease. In certain embodiments, the CKD is stage 4 chronic kidney disease. In certain embodiments, the CKD is stage 5 chronic kidney disease. In certain embodiments, the chronic kidney disease is pre-dialysis chronic kidney disease. In certain embodiments, the patient is a dialysis patient and these patients may be referred to as having end stage renal disease (ESRD). In certain such embodiments, the anemia, such as anemia secondary to CKD or ESRD may be refractory to treatment with an erythropoiesis stimulating agent, including a rhEPO product, such as, epoetin alfa, epoetin beta, darbepoetin, or peginesatide. In certain embodiments, the patient has been previously treated for anemia, while in certain alternative embodiments, the patient has not previously been treated for anemia.

In certain embodiments, the invention relates to methods of treating or preventing an angiogenesis-related disease or disorder, comprising administering to a patient having angiogenesis-related disease or disorder an effective amount of a solid form of Compound (I). In certain embodiments, the invention relates to methods of regulating angiogenesis, comprising administering to a patient an effective amount of a solid form of Compound (I).

In certain embodiments, the invention relates to methods of treating or preventing disease or disorder affected by the level of VEGF or GAPDH, comprising administering to a patient having a disease or disorder affected by the level of VEGF or GADPH an effective amount of a solid form of Compound (I).

In certain embodiments, the invention relates to methods of promoting wound healing, comprising administering to a patient having a wound an effective amount of a solid form of Compound (I).

In certain embodiments, the invention relates to methods of enhancing the revascularization of damaged tissue or increasing vasculature, comprising administering to a patient having damaged tissue an effective amount of a solid form of Compound (I). In certain embodiments, the invention relates to methods of vascularizing ischemic tissue, comprising administering to a patient having ischemic tissue an effective amount of a solid form of Compound (I).

In certain embodiments, the invention relates to methods of promoting the growth of skin graft replacements, comprising administering to a patient having a skin graft an effective amount of a solid form of Compound (I).

In certain embodiments, the invention relates to methods of promoting tissue repair in the context of guided tissue regeneration (GTR), comprising administering to a patient an effective amount of a solid form of Compound (I).

In certain embodiments, the invention relates to methods for treating a disease or condition related to diminished endogenous production of erythropoietin (EPO), comprising administering to a patient having a disease or condition related to diminished endogenous production of EPO a sufficient number of successive doses of a solid form of Compound (I) so as to raise the level of hemoglobin relative to a baseline hemoglobin level in a patient without significantly increasing the level of serum EPO relative to the baseline level of serum EPO.

In certain embodiments, the invention relates to methods for treating a disease or condition related to diminished endogenous production of erythropoietin (EPO), comprising administering to a patient having a disease or condition related to diminished endogenous production of EPO a sufficient number of successive doses of a solid form of Compound (I) so as to raise the level of hemoglobin relative to a baseline hemoglobin level in a patient without significantly increasing the level of serum EPO relative to the baseline level of serum EPO.

In certain embodiments, the invention relates to methods for treating a disease or condition related to diminished endogenous production of erythropoietin (EPO), comprising administering to a patient having a disease or condition related to diminished endogenous production of EPO a sufficient number of successive doses of a solid form of Compound (I) so as to raise the total iron binding capacity (TIBC) relative to a baseline TIBC in a patient, without significantly increasing the serum iron level relative to a baseline serum iron level.

In certain embodiments, the invention relates to methods for treating or preventing anemia in a subject, wherein the method comprises administering to the subject a pharmaceutically effective amount of solid form of Compound (I) while: a) restoring or maintaining the diurnal pattern of EPO serum levels; and/or b) maintaining pre-treatment levels of total iron (i.e., without increasing significantly the total iron levels); and/or c) not significantly decreasing hepcidin levels.

In certain embodiments, the invention relates to methods of treating a disease or condition selected from non-severe anemia secondary to chronic kidney disease, non-severe anemia secondary to congestive heart failure, and idiopathic anemia of aging, comprising administering to a patient having non-severe anemia secondary to chronic kidney disease, non-severe anemia secondary to congestive heart failure, or idiopathic anemia of aging a sufficient number of successive doses of a solid form of Compound (I) so as to raise the serum hemoglobin levels relative to a baseline serum hemoglobin level in a patient, without significantly decreasing hepcidin expression relative to a baseline hepcidin expression level.

In certain embodiments, the invention relates to methods of treating or preventing a disease or disorder selected from diabetic retinopathy, macular degeneration, cancer, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndrome, toxoplasmosis, trauma post-laser complications, diseases associated with rubeosis, and proliferative vitroeretinopathy, Crohn's disease and ulcerative colitis, psoriasis, sarcoidosis, rheumatoid arthritis, hemangiomas, Osler-Weber-Rendu disease, or hereditary hemorrhagic telangiectasia, solid or blood borne tumors, acquired immune deficiency syndrome, skeletal muscle and myocardial ischemia, stroke, coronary artery disease, peripheral vascular disease, and coronary artery disease, comprising administering to a patient having such a disease or disorder an effective amount of a solid form of Compound (I).

In certain embodiments, a solid form of Compound (I) may be administered according to a dosing regimen, such as that disclosed in U.S. application Ser. No. 61/834,808, filed in Jun. 13, 2013.

5.5 Combination Therapy

In certain embodiments, the invention relates to methods for treating anemia, such as anemia secondary to chronic kidney disease, comprising administering {[5-(3-chlorophenyl)-3-hydroxypyridine-2-carbonyl]amino}acetic acid in combination with another medicament. Such combination therapy may be achieved by way of the simultaneous, sequential, or separate dosing of the individual components of the treatment. Additionally, when administered as a component of such combination therapy, the {[5-(3-chlorophenyl)-3-hydroxypyridine-2-carbonyl]amino}acetic acid and the other medicament may be synergistic, such that the daily dose of either or both of the components may be reduced as compared to the dose of either component that would normally be given as a monotherapy. Alternatively, when administered as a component of such combination therapy, the {[5-(3-chlorophenyl)-3-hydroxypyridine-2-carbonyl]amino}acetic acid and the other medicament may be additive, such that the daily dose of each of the components is similar or the same as the dose of either component that would normally be given as a monotherapy.

In certain embodiments, the invention relates to methods for treating anemia, such as anemia secondary to chronic kidney disease, comprising administering a compound which is {[5-(3-chlorophenyl)-3-hydroxypyridine-2-carbonyl]amino}acetic acid to a patient having anemia, wherein the Compound (I) is optionally administered in combination with an iron supplement, such as ferrous sulfate, ferrous gluconate, or ferrous fumarate. In certain such embodiments, the iron supplement is administered at least one hour, at least two hours, at least three hours, at least four hours, or even at least six hours following administration of the compound. In certain embodiments, the iron supplement is administered in an amount such that ferritin is maintained at a level of between about 50 ng/mL and about 300 ng/mL. In certain embodiments, the iron supplement is administered orally at a daily dose of at least about 50 mg of elemental iron. In certain embodiments, the iron supplement is administered orally at a dose of about 50 mg of elemental iron. In certain embodiments, the iron supplement is administered intravenously. In certain embodiments, the iron supplement is administered continuously and/or indefinitely, such as for more than 42 consecutive days. In certain alternative embodiments, the iron supplement is administered on an as needed basis such that ferritin is maintained at a level of between about 50 ng/mL and about 300 ng/mL. In certain such embodiments, the daily dose of the Compound (I) is about 150 mg, about 300 mg, about 450 mg, about 600 mg, or about 750 mg of a solid form of Compound (I). In certain such embodiments, the daily dose is about 150 mg, about 300 mg, about 450 mg, or about 600 mg. Such daily doses may be administered orally, once daily, twice daily, or three times daily, preferably once daily.

In certain embodiments, the invention relates to methods for treating anemia, such as anemia secondary to chronic kidney disease, comprising administering a compound which is {[5-(3-chlorophenyl)-3-hydroxypyridine-2-carbonyl]amino}acetic acid to a patient having anemia, wherein the Compound (I) is optionally administered in combination with an erythropoiesis stimulating agent (ESA), such as an erythropoietin mimetic. In certain such embodiments, the ESA is an rhEPO product, including, but not limited to, epoetin alfa, epoetin beta, darbepoetin, or peginesatide. In certain such embodiments, the ESA is administered as a rescue therapy. In certain alternative embodiments, the ESA is administered continuously and/or indefinitely, such as for more than 42 consecutive days. In certain such embodiments, the daily dose is of the Compound (I) is about 150 mg, about 300 mg, about 450 mg, about 600 mg, or about 750 mg of a solid form of Compound (I). In certain such embodiments, the daily dose is about 150 mg, about 300 mg, about 450 mg, or about 600 mg. Such daily doses may be administered orally, once daily, twice daily, or three times daily, preferably once daily.

5.6 Pharmaceutical Compositions

Pharmaceutical compositions may be used in the preparation of individual, single unit dosage forms. Pharmaceutical compositions and dosage forms provided herein comprise a compound as provided herein, or a pharmaceutically acceptable salt, solvate, or hydrate thereof (e.g., the parent compound). Pharmaceutical compositions and dosage forms can further comprise one or more excipients.

In certain embodiments, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water.

Lactose-free compositions can comprise excipients that are well known in the art and are listed, for example, in the U.S. Pharmacopeia (USP) 25 NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients.

5.6.1 Oral Dosage Forms

Pharmaceutical compositions that are suitable for oral administration can be provided as discrete dosage forms, such as, but not limited to, tablets (e.g., chewable tablets), caplets, capsules, suspensions and liquids (e.g., flavored syrups). Such dosage forms contain predetermined amounts of active ingredients, and may be prepared by methods of pharmacy well known to those skilled in the art. See generally, Remington's The Science and Practice of Pharmacy, 21st Ed., Lippincott Williams & Wilkins (2005).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM. Other suitable forms of microcrystalline cellulose include, but are not limited to, silicified microcrystalline cellulose, such as the materials sold as PROSOLV 50, PROSOLV 90, PROSOLV HD90, PROSOLV 90 LM, and mixtures thereof.

Examples of fillers suitable for use in the pharmaceutical compositions and dosage forms provided herein include, but are not limited to, talc, microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form. The binder or filler in pharmaceutical compositions is, in another embodiment, present in from about 20 to about 30 weight percent of the pharmaceutical composition or dosage form. The binder or filler in pharmaceutical compositions is, in another embodiment, present in about 24 weight percent of the pharmaceutical composition or dosage form.

In certain embodiments, fillers may include, but are not limited to block copolymers of ethylene oxide and propylene oxide. Such block copolymers may be sold as POLOXAMER or PLURONIC, and include, but are not limited to POLOXAMER 188 NF, POLOXAMER 237 NF, POLOXAMER 338 NF, POLOXAMER 437 NF, and mixtures thereof. In certain embodiments, POLOXAMER or PLURONIC, including, but not limited to POLOXAMER 188 NF, POLOXAMER 237 NF, POLOXAMER 338 NF, POLOXAMER 437 NF, and mixtures thereof, are surfactants.

In certain embodiments, fillers may include, but are not limited to isomalt, lactose, lactitol, mannitol, sorbitol xylitol, erythritol, and mixtures thereof.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 5 to about 9 weight percent of disintegrant, or from about 1 to about 5 weight percent of disintegrant, or from about 1 to about 7 weight percent of disintegrant, or about 7 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, povidone, crospovidone, polacrilin potassium, sodium starch glycolate, potato or tapioca starch, other starches, pre-gelatinized starch, other starches, clays, other algins, other celluloses, gums, and mixtures thereof.

Glidants and/or lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium stearyl fumarate, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional glidants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic colloidal silicon dioxide product sold by Cabot Co. of Boston, Mass.), and mixtures thereof. If used at all, glidants and/or lubricants may be used in an amount of less than about 1 weight percent of the pharmaceutical compositions or dosage forms into which they are incorporated.

In certain embodiments, an oral dosage form comprises the compound, silicified microcrystalline cellulose, sodium starch glycolate, a block copolymer of ethylene oxide and propylene oxide, sodium stearyl fumarate and colloidal silicon dioxide. In certain embodiments, an oral dosage form comprises the Compound (I) in an amount of about 5% to about 75% by weight, silicified microcrystalline cellulose in an amount of about 15% to about 85%, sodium starch glycolate in an amount of about 2% to about 10%, block copolymer of ethylene oxide and propylene oxide in an amount of about 2% to about 10%, sodium stearyl fumarate in an amount of 0.2% to about 2%, and colloidal silicon dioxide in an amount of about 0.2% to about 2% by weight of the oral dosage form.

In certain embodiments, an oral dosage form comprises the compound, microcrystalline cellulose, isomalt, sodium starch glycolate, sodium lauryl sulfate, povidone, colloidal silicon dioxide, and magnesium stearate. In certain embodiments, an oral dosage form comprises the Compound (I) in an amount of about 40% to about 50%, microcrystalline cellulose in an amount of about 40% to about 50%, isomalt in an amount of 0% to about 5%, sodium starch glycolate in an amount of about 5% to about 10%, sodium lauryl sulfate in an amount of 0.2% to about 2%, povidone in an amount of about 2% to about 10%, colloidal silicon dioxide in an amount of 0.1% to about 1%, and magnesium stearate in an amount of about 0.1% to about 1% by weight of the oral dosage form.

In certain embodiments, the invention relates to unit dosage forms that comprise between about 100 mg and about 1,200 mg, about 200 mg and about 1,000 mg, about 400 mg and about 800 mg, or about 450 mg and about 600 mg of Compound (I).

In certain embodiments, the invention relates to unit dosage forms that comprise about 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1,000 mg, 1,050 mg, 1,100 mg, 1,150, or even about 1,200 mg of a solid form of Compound (I). In certain such embodiments, the unit dosage form is a capsule comprising about 40 mg, about 120 mg, about 185 mg, about 200 mg, about 200, about 250 mg, or even about 300 mg of a solid form of Compound (I). In certain such embodiments, the unit dosage form is a tablet comprising about 150 mg of a solid form of Compound (I). In certain such embodiments, the unit dosage form is a tablet comprising about 315 mg of a solid form of Compound (I).

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

6. EXAMPLES

The following examples are presented by way of illustration, not limitation. The following abbreviations are used in descriptions and examples:

ACN: Acetonitrile
Am: Amorphous
AS: ID for anti-solvent crystallization experiment
DCM: Dichloromethane
DIPEA: N,N-Diisopropylethylamine
DMA: Dimethylacetamide
DMF: N,N-Dimethylformide
DMSO: Dimethylsulfoxide
DSC: Differential Scanning calorimetry
DTA: Differential Thermal Analysis
DVS: Dynamic Vapor Sorption
EtOH: Ethanol
FBRM: Focussed Beam Reflectance Measurement
HPLC: High performance liquid chromatography
IPA: 2-Propanol
LCMS: Liquid Chromatography with Mass Spectroscopy
MEK: Methyl Ethyl Ketone
MeOH: Methanol
MiBK: Methyl isoButyl Ketone
mp: Melting point
MS: Mass spectrometry
MTBE: tert-Butyl methyl ether
MTBE: methyl tert-butyl ether
NMP: N-Methyl-2-pyrrolidone
NMP: N-methylpyrrolidinone
NMR: Nuclear magnetic resonance RH: Relative Humidity
RT: Room Temperature
S: Solvent
SDTA: Single Differential Thermal Analysis
SM: Starting material
TA: Thermal Analysis
TCP: ID for thermocycling and reflux experiment
TGA: Thermogravimetric Analysis
THF: Tetrahydrofuran
TLC: Thin layer chromatography
XRPD: X-Ray Powder Diffraction The following non-limiting examples show methods for generating Compound (I) with high purity by removing Compound (II),

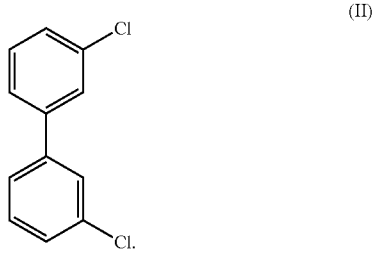 [SMILES: Clc1cccc(-c2cccc(Cl)c2)c1]

(II)

ChemDraw Ultra (Cambridgesoft, Cambridge, Mass.) was used to generate names for chemical structures.

6.1 Form A of Compound (I)

Precursor of Form A of Compound (I) (10.01 g, 0.033 mol) was charged into a 500 ml round bottom flask equipped with mechanical agitator, temperature probe and nitrogen line. 50 ml THF was charged into the 500 ml round bottom flask and the resulting mixture was agitated at room temperature until all solids dissolved. 50 g deionized water was charged into the 500 ml round bottom flask and the mixture was cooled down to 0-5° C.

A sodium hydroxide solution was prepared by mixing 6.65 g of 50% by weight aqueous sodium hydroxide solution with 50 g water. The prepared sodium hydroxide solution was charged into the 500 ml round bottom flask slowly while the temperature of the mixture was maintained between 0 and 5° C. The pH of the mixture was 13 after addition of the prepared sodium hydroxide solution. The mixture was warmed up to 19-25° C. and agitated for 1 to 2 hours (the mixture may be agitated longer).

37% by weight concentrated aqueous HCl solution was added slowly into the reaction mixture until the pH of the reaction mixture reached 5, while the temperature of the reaction mixture was maintained below 25° C. About 8.5 g 37% by weight concentrated aqueous HCl solution was used.

The mixture was then concentrated to about 60 ml (55 to 65 ml is recommended). Additional 50 g deionized water was added and the mixture was agitated for about 2 hours.

Solids were collected from the mixture by filtration and washed with 20 g deionized water. The solid material was air dried until transferrable. The weight of the dried solid was 13.4 g. The HPLC analysis indicated that the purity of the solid was 99.46% (area %).

6.1.1 Hot Water Trituration of Form A of Compound (I)

The solid material obtained in section 6.1 was charged into to a 500 ml round bottom flask equipped with mechanical agitator, temperature probe and nitrogen line. 70 g deionized water was charged into the 500 ml round bottom flask and the resulting mixture was agitated at 70-80° C. for 16 hours. After the mixture was cooled down to room temperature, solids were collected from the mixture by filtration and washed by 20 g deionized water. The solid material was air dried until transferrable.

6.1.2 Charcoal Treatment and Recrystallization of Form A of Compound (I)

The solid material obtained in section 6.1 was charged into to a 500 ml round bottom flask equipped with mechanical agitator, temperature probe and nitrogen line. 130 g acetone was charged into the 500 ml round bottom flask and the resulting mixture was agitated at room temperature until all solids dissolved (ca. 30 minutes). If the solids did not dissolve completely, more acetone was added. The resulting solution was treated with activated carbon. The activated carbon was then removed by filtration and the resulting acetone solution was concentrated to about 73 ml (70 to 75 ml is recommended). The concentrated acetone solution was heated to reflux. While keeping the solution below 50° C., 65 g water was added slowly. Precipitation of a light colored solid was observed. The mixture was cooled down to 22° C. (between 19 to 25° C.) over ca. 2 hours and agitated at 22° C. for ca. 2 to 3 hours. Solids were collected from the mixture by filtration and washed with a mixture of 11.5 g acetone and 15 g deionized water. The solid material was air dried for at least 6 hours. The weight of the dried solid material was 9.2 g. The HPLC analysis indicated the purity of the solid was 99.71% (area %).

6.2 Solid Form A of Compound (I)

6.2.1 Characterization of Form A of Compound (I)

XRPD analysis as depicted in FIG. 1 shows Form A to be predominantly crystalline with sharp, distinct peaks up to 40°2θ on a reasonably flat baseline. The raised background from ca. 8° to 16° 2θ is a known artifact due to the sample holder. A list of X-Ray Diffraction Peaks for Form A of Compound (I) is provided below in Table 1.

TABLE 1

| X-Ray Diffraction Peaks for Form A of Compound (I) | |
|---|---|
| Two-theta angle (°) | Relative Intensity (%) |
| 9.8 | 3.2 |
| 11.0 | 1.9 |
| 13.3 | 1.1 |
| 14.6 | 2.5 |
| 14.8 | 5.5 |
| 15.0 | 12.7 |
| 16.3 | 5.7 |
| 16.4 | 2.5 |
| 16.9 | 9.1 |
| 18.1 | 14.5 |
| 18.6 | 11.0 |
| 19.7 | 9.9 |
| 20.3 | 46.2 |
| 22.0 | 3.2 |
| 22.9 | 53.7 |
| 23.3 | 3.5 |
| 24.0 | 31.4 |
| 24.2 | 11.4 |
| 25.2 | 11.3 |
| 25.7 | 3.5 |

TABLE 1-continued

X-Ray Diffraction Peaks for Form A of Compound (I)

| Two-theta angle (°) | Relative Intensity (%) |
|---|---|
| 25.9 | 8.4 |
| 26.3 | 100.0 |
| 26.8 | 12.8 |
| 27.6 | 6.8 |
| 28.3 | 1.5 |
| 28.9 | 1.0 |
| 29.6 | 8.9 |
| 29.8 | 1.4 |
| 30.3 | 0.5 |
| 31.3 | 1.2 |
| 32.2 | 1.2 |
| 32.9 | 2.4 |
| 34.1 | 7.0 |
| 34.9 | 1.8 |
| 35.2 | 12.9 |
| 35.7 | 1.4 |
| 36.2 | 0.5 |
| 36.7 | 1.2 |
| 37.2 | 3.8 |
| 37.4 | 11.4 |
| 37.7 | 3.4 |
| 38.3 | 1.0 |
| 38.6 | 1.3 |
| 38.9 | 1.2 |

Figure 2:
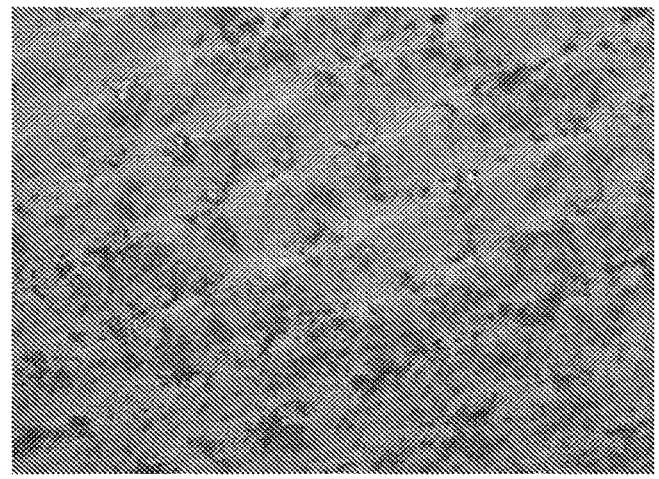
FIG. 2 shows a polarized light microscopy (PLM) analysis of Compound (I), Form A.
Figure 2:
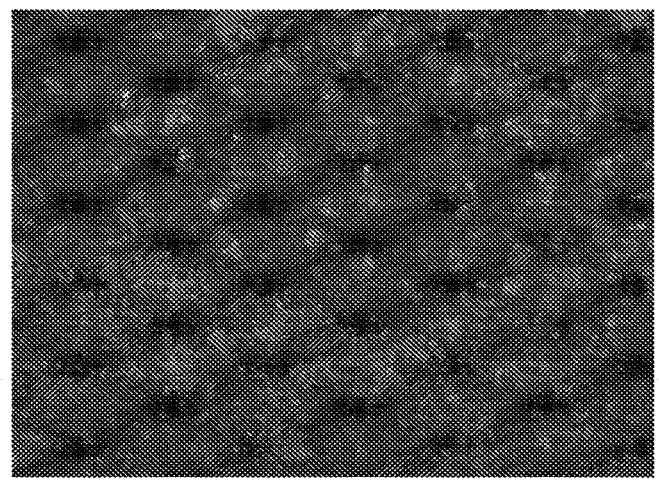

PLM analysis as depicted in FIG. 2 shows some birefringence under polarised light; however the crystals are very small with no clearly defined morphology.

TGA analysis as depicted in FIG. 3 shows negligible weight loss from ambient temperature, and then significant weight loss above ca. 220° C. which is consistent with decomposition. DTA analysis as depicted in FIG. 3 shows a single sharp endotherm with an onset of 171.5° C.

DSC analysis as depicted in FIG. 4 shows a single sharp endotherm with an onset at 172.4° C. and a peak at 175.8° C.

Figure 5:
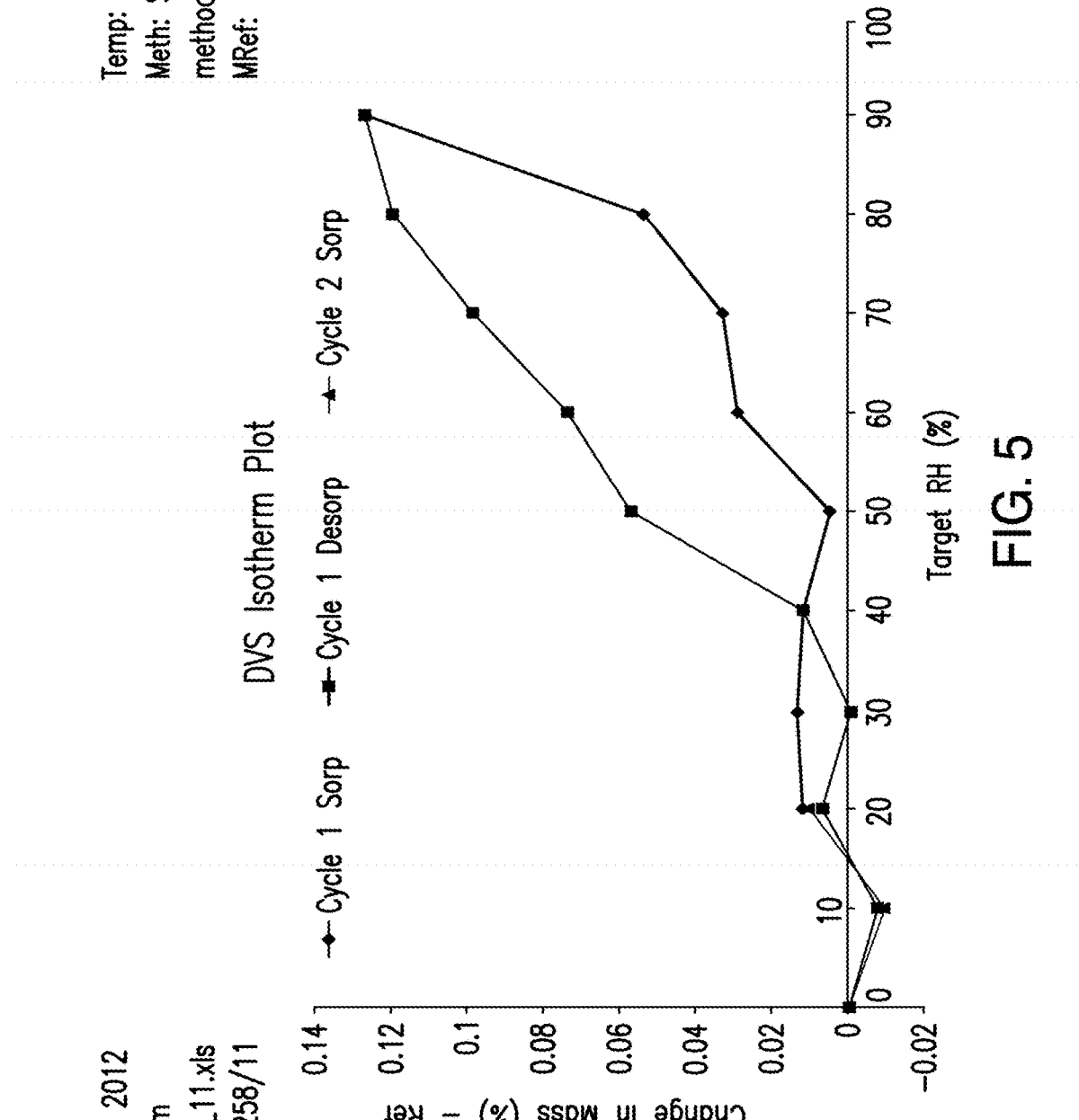
FIG. 5 shows a dynamic vapor sorption (DVS) isotherm plot of Compound (I), Form A.
Figure 6:
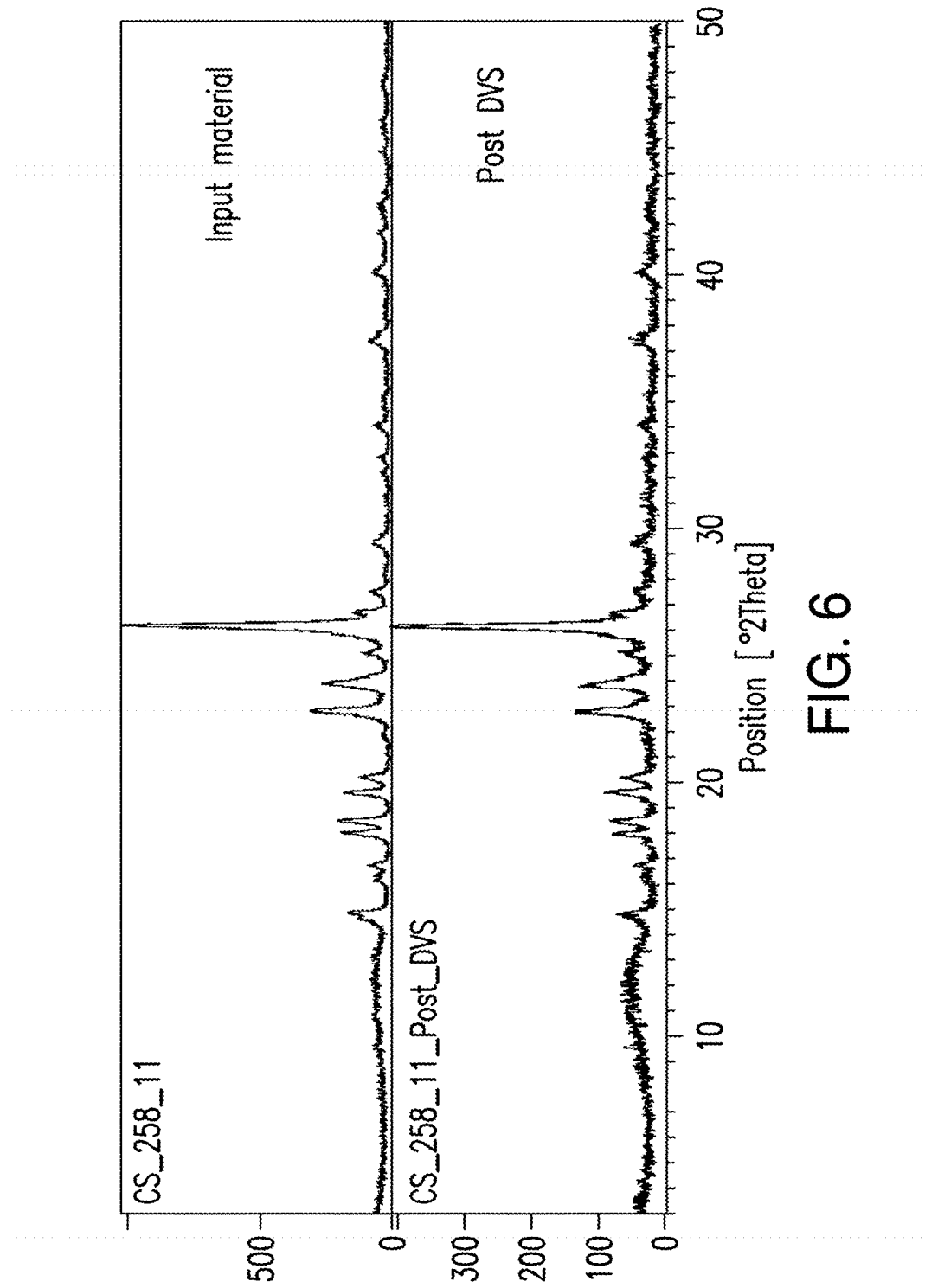
FIG. 6 shows the pre and post DVS XRPD analysis of Compound (I), Form A.

DVS analysis as depicted in FIG. 5 shows that water sorption at 90% RH is 0.13% indicating that the material is non-hygroscopic. XRPD analysis following DVS as depicted in FIG. 6 shows no change in form.

Figure 7:
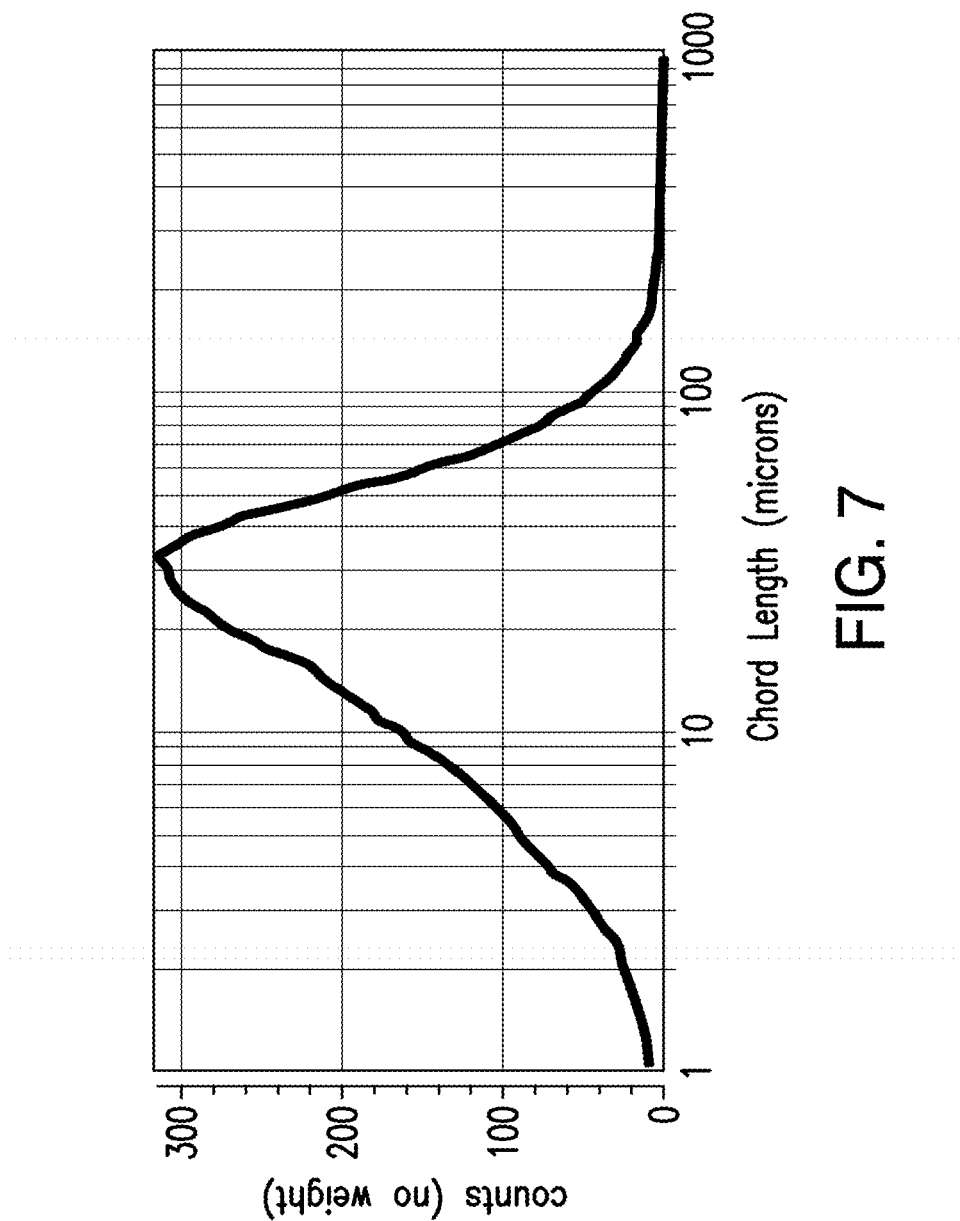
FIG. 7 shows the particle size analysis of Compound (I), Form A.

The FBRM data as depicted in FIG. 7 shows the material to consist of small particles with the majority being less than 100 μm as illustrated in the non-weighted distribution.

Figure 8:
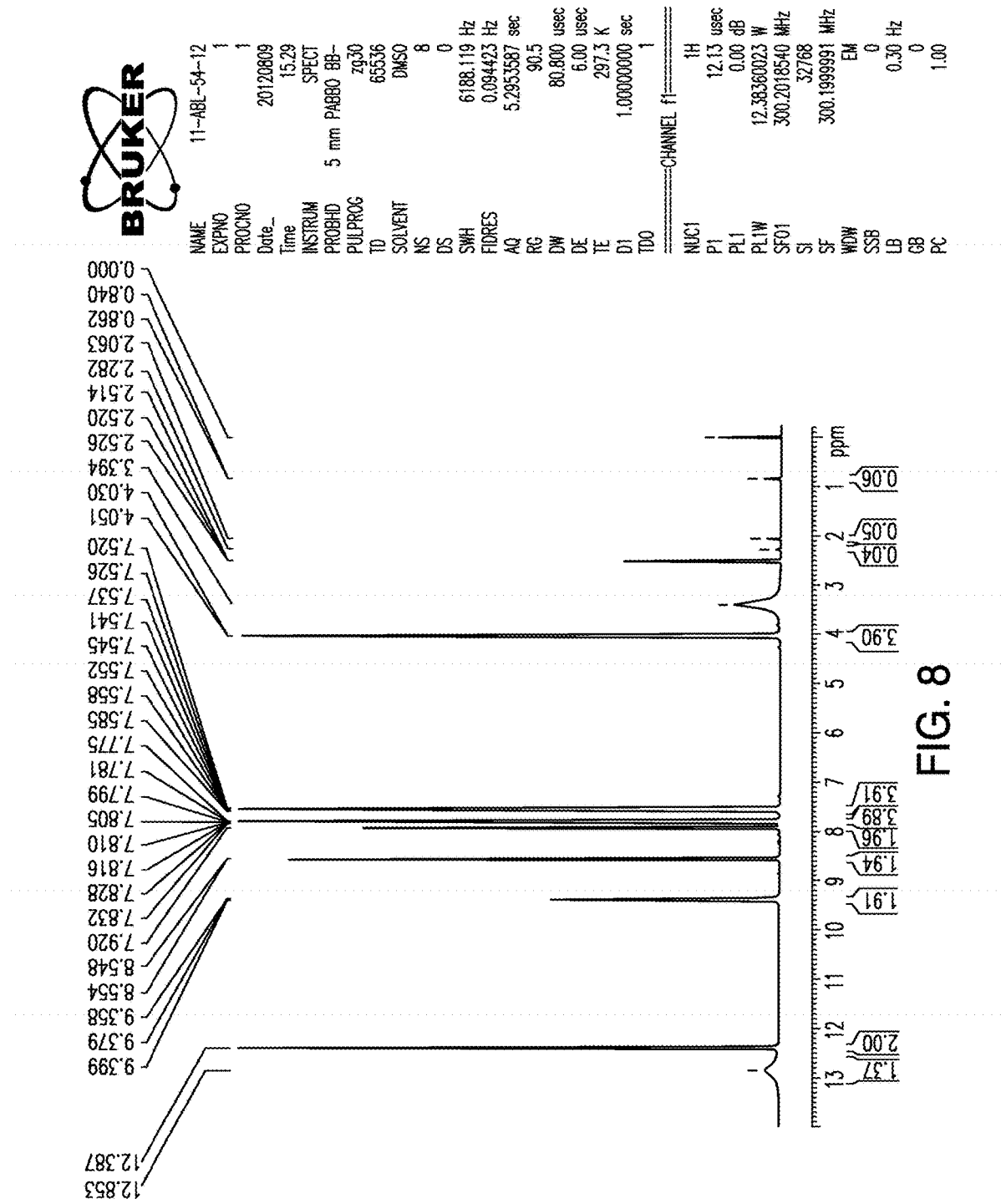
FIG. 8 shows the $^1$H NMR spectrum of Compound (I), Form A.
Figure 9:
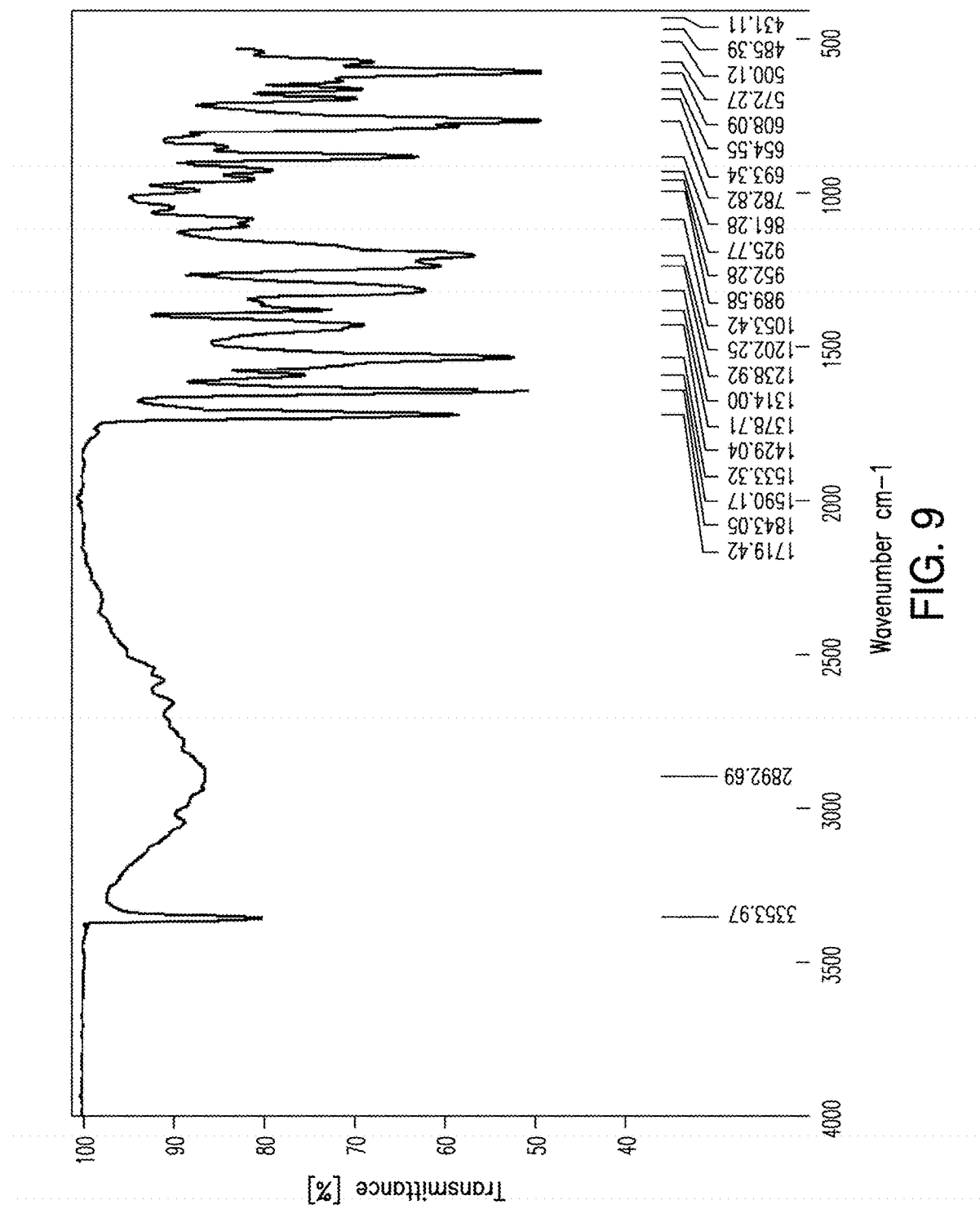
FIG. 9 shows the IR spectrum of Compound (I), Form A.

The solution NMR spectrum as depicted in FIG. 8 is consistent with the structure of Compound (I). The IR absorption spectrum is provided in FIG. 9.

Figure 10:
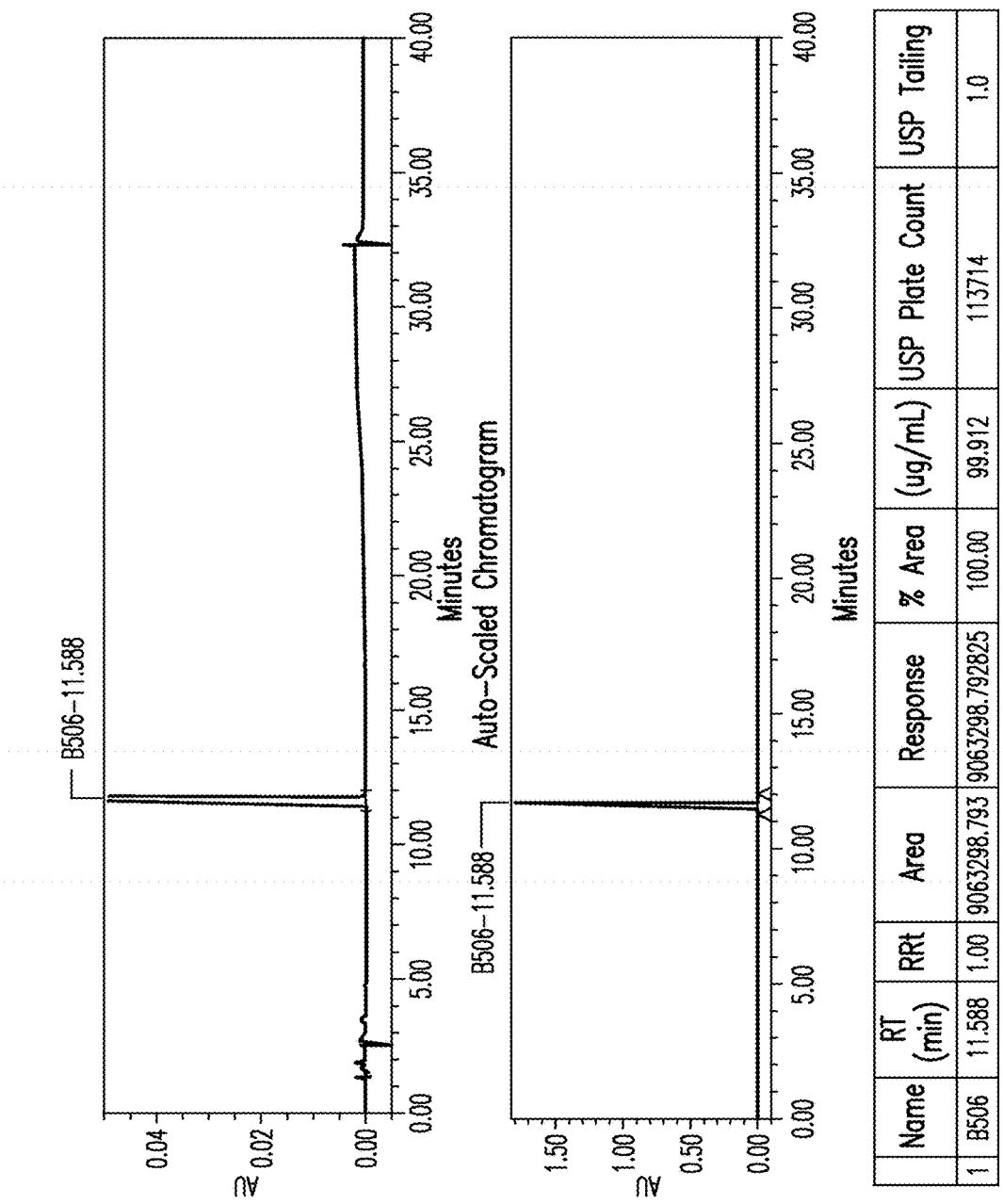
FIG. 10 shows the HPLC analysis of Compound (I), Form A.

HPLC analysis as depicted in FIG. 10 indicates that the sample purity as shown in Table 2.

TABLE 2

HPLC purity of Form A of Compound (I)

| Peak Number | Retention Time (minutes) | Area (%) |
|---|---|---|
| 1 | 11.588 | 100.00 |

6.2.2 Solubility Experiments

Approximately 20 mg of Form A of Compound (I) was placed in each of 48 vials and 5 volume aliquots of the appropriate solvent systems were added to the appropriate vial. Between each addition, the mixture was checked for dissolution and if no dissolution was apparent, the mixture was warmed to ca. 50° C. and checked again. This procedure was continued until dissolution was observed or until 100 volumes of solvent had been added. The approximate solubilities are shown in Table 3.

TABLE 3

Solvent List for solubility experiment

| Solvent | Solubility (mg/mL) RT (ca. 22° C.) | Solubility (mg/mL) (ca. 50° C.) |
|---|---|---|
| Acetone | 100 | >100 |
| Acetone/Water (3%) | <200 | 200 |
| Acetone/Water (20%) | <200 | 200 |
| Acetonitrile | <13 | 13 |
| Anisole | <40 | 40 |
| Benzonitrile | <10 | <10 |
| Benzyl alcohol | <68 | 68 |
| 1-Butanol (1-BuOH) | <20 | 20 |
| Chloroform | <10 | <10 |
| Cyclohexane | <10 | <10 |
| Cyclohexanone | <200 | 200 |
| Cumene | <10 | <10 |
| Dichloromethane (DCM) | <10 | <10 |
| Diethyl ether | <10 | 10 |
| Diisopropyl ether (DIPE) | <10 | <10 |
| Dimethylacetamide (DMA) | >200 | >200 |
| Dimethylformamide (DMF) | >200 | >200 |
| Dimethyl sulfoxide (DMSO) | >200 | >200 |
| 1,4-Dioxane | >200 | >200 |
| Ethanol (EtOH) | 34 | >34 |
| 2-Ethoxyethanol | <200 | 200 |
| Ethyl acetate (EtOAc) | <41 | 41 |
| EtOAc/Cyclohexane (1:2) | <10 | <10 |
| EtOAc/Toluene (1:2) | <14 | 14 |
| Ethylene glycol | <10 | <10 |
| Heptane | <10 | <10 |
| Isobutyl acetate (iBuOAc) | <20 | 20 |
| Isopropyl acetate (iPrOAc) | <26 | 26 |
| Methanol (MeOH) | <51 | 51 |
| MeOH/Water (1%) | <40 | 40 |
| MeOH/Water (20%) | <10 | <10 |
| MeOH/Water (50%) | <10 | <10 |
| 2-Methoxyethanol | >200 | >200 |
| Methyl acetate (MeOAc) | <68 | 68 |
| 3-Methyl-1-butanol | <10 | <10 |
| Methyl ethyl ketone (MEK) | <100 | 100 |
| Methyl isobutyl ketone (MIBK) | <34 | 34 |
| 2-Methyl tetrahydrofuran (2-MeTHF) | >200 | >200 |
| Nitromethane | <10 | <10 |
| N-methyl-2-pyrrolidone (NMP) | >200 | >200 |
| 1,2-Propanediol | <20 | 20 |
| 1-Propanol (1-PrOH) | <20 | 20 |
| 2-Propanol (IPA) | <13 | 13 |
| methyl tert-butyl ether (MTBE) | 14 | >14 |
| Tetrahydrofuran (THF) | >200 | >200 |
| Toluene | <10 | <10 |
| Trifluoroethanol (TFE) | <10 | <10 |
| Water | <10 | <10 |

6.2.3 Analysis Methods

XRPD analysis was conducted on a Siemens D5000, scanning the samples between 3 and 50 °2θ. Approximately, 5 mg or less (material dependant) of sample was gently compressed on a glass disc inserted into an XRPD sample holder. The sample was then loaded into a Siemens D5000 diffractometer running in reflection mode and analysed, using the following experimental conditions in Table 4. A calibration check was performed on the Siemens D5000 XRPD on a monthly basis using the Alumina Powder Standard Reference Material 676a.

TABLE 4

X-ray Powder Diffraction (XRPD) experiemental conditions

| Raw Data Origin | Siemens-binary V2 (.RAW) |
|---|---|
| Start Position [°2θ] | 3.0000 |
| End Position [°2θ] | 40.000 |
| Step Size [°2θ] | 0.0200 |
| Scan Step Time [s] | 1 |
| Scan Type | Continuous |
| Offset [°2θ] | 0.0000 |
| Divergence Slit Type | Fixed |
| Divergence Slit Size [°] | 2.0000 |
| Specimen Length [mm] | various |
| Receiving Slit Size [mm] | 0.2000 |
| Measurement Temperature [° C.] | 20.00 |
| Anode Material | Cu |
| K-Alpha1 [Å] | 1.54060 |
| K-Alpha2 [Å] | 1.54443 |
| K-Beta [Å] | 1.39225 |
| K-A2/K-A1 Ratio | 0.50000 (nominal) |
| Generator Settings | 40 mA, 40 kV |
| Diffractometer Type | d5000 |
| Diffractometer Number | 0 |
| Goniometer Radius [mm] | 217.50 |
| Incident Beam Monochromator | No |
| Diffracted Beam Monochromator | (Graphite) |
| Spinning | No |

It should be understood that the numerical values of the peaks of an X-ray powder diffraction pattern may vary slightly from one machine to another or from one sample to another, and so the values quoted are not to be construed as absolute, but with an allowable variability, such as ±0.2 degrees 2 theta (see e.g., Remington's Pharmaceutical Sciences, 22nd ed., Pharmaceutical Press, (2012); The United States Pharmacopoeia, 30th ed., (2011)).

Polarised Light Microscopy (PLM) was conducted on an Olympus BX50 polarising microscope, equipped with a Motic camera and image capture software (Motic Images Plus 2.0). All images were recorded using the 20× objective, unless otherwise stated.

Thermal Gravimetric/Differential Thermal Analysis (TG/DTA) were performed on a simultaneous thermogravimetric/differential thermal analyser. Approximately 5 mg or less (material dependant) was accurately weighed into an open aluminium pan and loaded into the analyser and held at room temperature. The sample was then heated at a rate of 10° C./min from 25° C. to 300° C. during which time the change in sample weight was recorded along with any differential thermal events (DTA). Nitrogen was used as the purge gas, at a flow rate of 100 cm$^3$/min. The TGA furnace was cleaned by burn-out on a monthly basis prior to a temperature check using an Indium reference standard. A weight check was also performed on a monthly basis. DSC data can vary with scan rate and sample pan configuration.

Differential Scanning Calorimetry (DSC) was performed on a Seiko DSC6200 equipped with a cooler. Approximately 5 mg or less (material dependant) was accurately weighed into an aluminium DSC pan and sealed non-hermetically with a pierced aluminium lid. The sample pan was then loaded into the Seiko DSC6200 cooled and held at 25° C. Once a stable heat-flow response was obtained, the sample and reference were heated to ca. 220° C. at scan rate of 10° C./min and the resulting heat flow response monitored. A monthly temperature check was performed using an Indium reference standard.

Dynamic Vapour Sorption (DVS) was performed on a DVS-1 dynamic vapour sorption balance by Surface Measurement Systems. Approximately 10-20 mg of sample was loaded into a wire mesh vapour sorption balance pan of the balance. The sample was subjected to a ramping profile from 20-90% relative humidity (RH) in 10% increments, maintaining the sample at each step until a stable weight had been achieved (99.5% step completion) or 1000 minutes had elapsed. After completion of the sorption cycle, the sample was dried using the same procedure, but all the way down to 0% RH and finally taken back to the starting point of 20% RH. The weight change during the sorption/desorption cycles were plotted, allowing for the hygroscopic nature of the sample to be determined. Following the DVS analysis, the solid was re-analysed by XRPD in order to determine whether there had been any change in physical form.

Focussed Beam Reflectance Measurement (FBRM) was carried out using a Mettler Toledo D600 probe for particle size analysis. The probe was placed into a suspension of the material in ca. 200 ml acetonitrile and chord length distributions with various count statistics were monitored over a few minutes, while the sample was being stirred. A quarterly performance verification was carried out on the FBRM using a PVC reference standard and a fixed beaker stand. FBRM data can vary depending on solubility in the solvent system used.

Infrared Spectroscopy (IR) was carried out on a Bruker ALPHA P spectrometer. Sample material was placed onto the centre of a plate on the spectrometer and the spectra were obtained directly from the material (i.e. no KBr disc) using the following parameters in Table 5. An internal performance quality check on the IR spectrometer was performed on a monthly basis.

TABLE 5

Infrared Spectroscopy (IR) experiemental conditions

| Resolution | 4 cm$^{-1}$ |
|---|---|
| Background Scan Time | 16 scans |
| Sample Scan Time | 16 scans |
| Data Collection | 4000 to 400 cm$^{-1}$ |
| Result Spectrum | Transmittance |
| Software | OPUS version 6 |

$^1$H Nuclear Magnetic Resonance ($^1$H NMR) experiements were performed on a Bruker AV400 ($^1$H frequency: 400 MHz). $^1$H NMR experiments of each sample were performed in DMSO-d$_6$ and samples were prepared to ca. 1 mg/mL concentration.

High Performance Liquid Chromatography (HPLC) was performed according to the conditions in Table 6 and gradient program in Table 7.

TABLE 6

High Performance Liquid Chromatography (HPLC) experiemental conditions

| Sample Preparation | 0.6 mg/mL prepared in water/acetonitrile; 1/1; v/v |
|---|---|
| Instrument | Agilent 1100 |
| Column | Waters Symmetry Shield RP18 |
| | 150 × 4.6 mm; 5 μm |
| Column Temperature | 30° C. |
| λ | 263 nm |
| Injection Volume | 5 μl |
| Flow Rate | 1 ml/min |
| Mobile Phase A | Water/acetonitrile/TFA; 950/50/1; v/v/v |
| Mobile Phase B | Acetonitrile/water/TFA; 950/50/1; v/v/v |
| Run Time | 40 minutes |
| Integration Time | 30 minutes |
| Wash Vial | Water/acetonitrile; 1/1; v/v |

TABLE 7

High Performance Liquid Chromatography (HPLC) experiemental gradient program

| Time (mins) | % A | % B |
|---|---|---|
| 0 | 100 | 0 |
| 25 | 0 | 100 |
| 30 | 0 | 100 |
| 30.01 | 100 | 0 |
| 40 | 100 | 0 |

6.3 Solid Form B of Compound (I)

Solid Form B of Compound (I) was prepared by weighing approximately 600 mg of Compound (I) into a 100 mL Duran flask and dissolving in approximately 40 mL of acetonitrile. The solution was then filtered into a clean 100 mL glass beaker and placed in a dessicator under vacuum until all solvent had been removed. XRPD analysis as depicted in FIG. 11 shows Form B to be predominantly crystalline with sharp, distinct peaks up to 40°2θ on a reasonably flat baseline. The raised background from ca. 8° to 16° 2θ is a known artifact due to the sample holder.

TGA analysis of Form B showed a small weight loss of 1.2% between 100° C. and 130° C., then significant weight loss above ca. 220° C. DTA showed an event(s) between 120° C. and 135° C. (which corresponds to the weight loss by TGA), however it was indistinct. There was a main, sharp endotherm having an onset of 171.5° C. and a peak at 175.7° C.

DSC analysis showed a small exotherm with an onset at 109.2° C. and a peak at 113.7° C., followed by a main, sharp endotherm with an onset at 173.4° C. and a peak at 176.2° C.

DVS analysis showed that water sorption at 90% RH was 0.33% indicating that the material is non-hygroscopic. XRPD analysis following DVS showed no change in form.

Form B exhibits good qualities such as crystallinity and high melting point, along with being anhydrous and non-hygroscopic. However, Form B is metastable and can convert to Form A in slurries at high temperature.

6.4 Solid Form C of Compound (I)

An approximately 22% (g/ml) solution of Compound (I) in 2-methyltetrahydrofuran was adjusted to approximately 7% (g/mL) solution of Compound (I) in 2-methyltetrahydrofuran by adding n-heptane in not less than 30 minutes. at 40-50° C. The suspension was stirred at 40-50° C. for not less than 1 hour, followed by slow cooling to 0-10° C. The suspension was stirred out for not less than 1 hour at 0-10° C. and filtered. The wet cake was washed with cold n-heptane/2-methyltetrahydrofuran (6:1) and dried at not more than 50° C. under vacuum, yielding Form C as white crystals. XRPD analysis as depicted in FIG. 12 shows Form C to be predominantly crystalline with sharp, distinct peaks up to 40°2θ on a reasonably flat baseline.

6.5 Pharmaceutical Compositions

6.5.1 40 mg, 200 mg, and 300 mg Capsule Formulations

Capsule formulations can be prepared as follows:

| Material | Capsule, 40 mg | Capsule, 200 mg | Capsule 300 mg |
|---|---|---|---|
| Form A of Compound (I) (parent) | 40 mg | 200 mg | 300 mg |
| ProSolv ® HD 90 | 464.5 mg | 224.8 mg | 124.8 mg |
| Explotab ® sodium starch glycolate, NF | 28.5 mg | 24.0 mg | 24.0 mg |
| Poloxamer 188 NF | 28.5 mg | 24.0 mg | 24.0 mg |
| PRUV ® | 5.7 mg | 4.8 mg | 4.8 mg |
| Cab-O-Sil M-5P | 2.85 mg | 2.40 mg | 2.40 mg |
| Total | 570 mg | 480.0 mg | 480.0 mg |

6.5.2 120 mg, 185 mg, 250 mg, and 315 Capsule Formulations

Capsule formulations can be prepared as follows:

| Material | Capsule, 120 mg | Capsule, 185 mg | Capsule, 250 mg | Capsule, 315 mg |
|---|---|---|---|---|
| Form A of Compound (I) (parent) | 120.00 mg | 185.00 mg | 250.00 mg | 315.00 mg |
| ProSolv ® HD 90 | 304.80 mg | 239.80 mg | 173.60 mg | 107.40 mg |
| Explotab ® sodium starch glycolate, NF | 24.00 mg | 24.00 mg | 24.00 mg | 24.00 mg |
| Poloxamer 188 NF | 24.00 mg | 24.00 mg | 24.00 mg | 24.00 mg |
| PRUV ® | 4.80 mg | 4.80 mg | 4.80 mg | 4.80 mg |
| Cab-O-Sil M-5P | 2.40 mg | 2.40 mg | 3.60 mg | 4.80 mg |
| Total | 480.00 mg | 480.00 mg | 480.00 mg | 480.00 mg |

6.5.3 150 mg Tablet Formulation

A tablet formulation can be prepared as follows:

| Material | Excipient Grade | Quantity (mg) |
|---|---|---|
| Intra-granular Components | | |
| Form A of Compound (I) (parent) | — | 150.0 |
| Microcrystalline Cellulose, USP/NF | Avicel ® PH105 | 158.4 |
| Isomalt, USP/NF | Galen IQ 801 | 9.53 (9.521) |
| Explotab ® sodium starch glycolate, NF | Explotab ® | 10.70 (or 10.71) |
| Sodium Lauryl Sulfate, NF | — | 3.57 |
| Povidone, USP/NF | Kollidon ®25 | 8.92 (8.925) |
| Purified Water or Water for Injection, USP[1] | — | As required |

-continued

| Material | Excipient Grade | Quantity (mg) |
|---|---|---|
| Extra-granular Components | | |
| Explotab ® sodium starch glycolate, NF | Explotab ® | 14.28 |
| Colloidal Silicon Dioxide, NF | Cab-O-Sil | 0.89 |
| Magnesium Stearate, NF | Hyqual ® 5712 | 0.71 (0.714) |
| Total | | 357.0 |

Abbreviations:
NF = National Formulary,
USP = United States Pharmacopeia
[1]Removed during processing

6.5.4 315 mg Tablet Formulation

A 315 mg tablet formulation can be prepared as follows using a wet granulation process:

| Material | Excipient Grade | Quantity (mg) |
|---|---|---|
| Intra-granular Components | | |
| Form A of Compound (I) (parent) | | 315.0 |
| Microcrystalline cellulose, USP/NF | Avicel ® PH105 | 317.9 |
| Isomalt, USP/NF | Galen IQ 801 | 20.00 |
| Explotab ® sodium starch glycolate, NF | Explotab ® | 22.50 |
| Sodium lauryl sulfate, NF | | 7.500 |
| Povidone, USP/NF | Kollidon ® 25 | 33.75 |
| Purified water for Injection, USP | | As required |
| Extra-granular Components | | |
| Explotab ® sodium starch glycolate, NF | Explotab ® | 30.00 |
| Colloidal Silicon Dioxide, NF | Cab-O-Sil | 1.875 |
| Magnesium Stearate, NF | Hyqual ® 5712 | 1.5 |
| Total | | 750.0 |

6.5.5 Alternative 315 mg Tablet Formulation

A 315 mg tablet formulation may be prepared as follows using a wet granulation process:

| Material | Excipient Grade | Quantity (mg) |
|---|---|---|
| Intra-granular Components | | |
| Form A of Compound (I) (parent) | | 315.0 |
| Microcrystalline cellulose, USP/NF | Avicel ® PH105 | 317.9 |
| Explotab ® sodium starch glycolate, NF | Explotab ® | 22.50 |
| Sodium lauryl sulfate, NF | | 7.500 |
| Povidone, USP/NF | Kollidon ® 25 | 33.75 |
| Purified water for Injection, USP | | As required |
| Extra-granular Components | | |
| Explotab ® sodium starch glycolate, NF | Explotab ® | 30.00 |
| Colloidal Silicon Dioxide, NF | Cab-O-Sil | 1.875 |
| Magnesium Stearate, NF | Hyqual ® 5712 | 1.5 |
| Total | | 730.0 |

6.5.6 100 mg Tablet Formulation

A 100 mg tablet formulation may be prepared as follows using a wet granulation process:

| Material | Excipient Grade | Quantity (mg) |
|---|---|---|
| Intra-granular Components | | |
| Form A of Compound (I) (parent) | | 100.0 |
| Microcrystalline Cellulose, USP/NF | Avicel ® PH105 | 105 (105.6) |
| Isomalt, USP/NF | Galen IQ 801 | 6.5 (or 6.4) |
| Explotab ® sodium starch glycolate, NF | Explotab ® | 7.1 |
| Sodium Lauryl Sulfate, NF | | 2.4 |
| Povidone, USP/NF | Kollidon ®25 | 5.9 |
| Purified Water or Water for Injection, USP[1] | | As required |
| Extra-granular Components | | |
| Explotab ® sodium starch glycolate, NF | Explotab ® | 9.5 |
| Colloidal Silicon Dioxide, NF | Cab-O-Sil | 0.6 |
| Magnesium Stearate, NF | Hyqual ® 5712 | 0.5 |
| Total | | 237.5 (or 238.0) |

Abbreviations:
NF = National Formulary,
USP = United States Pharmacopeia
[1]Removed during processing

6.5.7 250 mg Tablet Formulation

A 250 mg tablet formulation may be prepared as follows using a wet granulation process:

| Material | Excipient Grade | Quantity (mg) |
|---|---|---|
| Intra-granular Components | | |
| Form A of Compound (I) (parent) | | 250.0 |
| Microcrystalline Cellulose, USP/NF | Avicel ® PH105 | 263 (or 264) |
| Isomalt, USP/NF | Galen IQ 801 | 15.8 (or 15.9) |
| Explotab ® sodium starch glycolate, NF | Explotab ® | 17.8 |
| Sodium Lauryl Sulfate, NF | | 5.9 |
| Povidone, USP/NF | Kollidon ®25 | 16.0 (or 14.9) |
| Purified Water or Water for Injection, USP[1] | | As required |
| Extra-granular Components | | |
| Explotab ® sodium starch glycolate, NF | Explotab ® | 23.8 |
| Colloidal Silicon Dioxide, NF | Cab-O-Sil | 1.5 |
| Magnesium Stearate, NF | Hyqual ® 5712 | 1.2 |
| Total | | 595.0 |

Abbreviations:
NF = National Formulary,
USP = United States Pharmacopeia
[1]Removed during processing

What is claimed is:
1. Crystalline Compound (I):

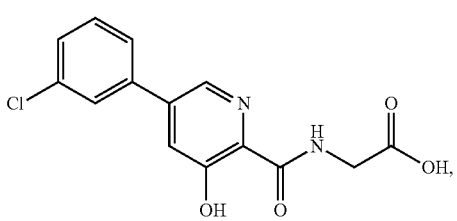

(I)

which has an X-ray powder diffraction pattern comprising peaks at 18.1, 20.3, 22.9, 24.0, and 26.3±0.2° 2θ.

2. The crystalline compound (I) of claim 1, wherein the crystalline compound comprises less than 10% by weight of any other crystalline Compound (I).

3. The crystalline compound (I) of claim 2, wherein the crystalline compound (I) comprises less than 5% by weight of any other crystalline Compound (I).

4. The crystalline compound (I) of claim 1, wherein the crystalline compound comprises less than 10% by weight of amorphous Compound (I).

5. The crystalline compound (I) of claim 4, wherein the crystalline compound (I) comprises less than 5% by weight of amorphous Compound (I).

6. The crystalline compound (I) of claim 1, which has a DSC endotherm at about 175.8° C.

7. The crystalline compound (I) of claim 1, wherein the crystalline compound (I) comprises less than 100 ppm of a compound of Formula (II),

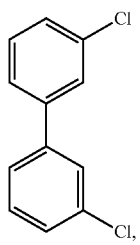

(II)

as determined by GC/MS.

8. The crystalline compound (I) of claim 7, wherein the crystalline compound (I) comprises less than 50 ppm of a compound of Formula (II).

9. The crystalline compound (I) of claim 8, wherein the crystalline compound (I) comprises less than 10 ppm of a compound of Formula (II).

10. The crystalline Compound (I) of claim 1, wherein the crystalline Compound (I) is at least 99.5% pure as measured by HPLC.

11. A pharmaceutical composition comprising the crystalline compound (I) of claim 1.

12. An oral dosage form comprising the crystalline compound (I) of claim 1.

13. Crystalline Compound (I),

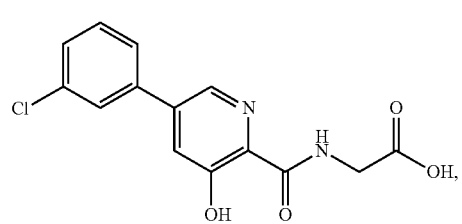

(I)

which has an X-ray powder diffraction pattern as shown in FIG. 1.

14. A pharmaceutical composition comprising the crystalline compound (I) of claim 13.

15. Crystalline Compound (I),

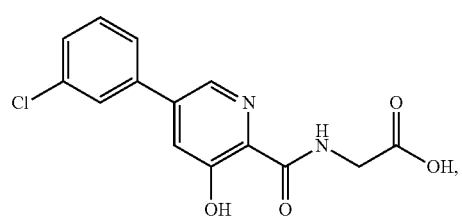

(I)

prepared by crystallization from a solution comprising acetone and Compound (I).

16. The crystalline compound (I) of claim 15, which has an X-ray powder diffraction pattern comprising peaks at 18.1, 20.3, 22.9, 24.0, and 26.3±0.2° 2θ.

17. The crystalline compound (I) of claim 16, which has a DSC endotherm at about 175.8° C.

18. A pharmaceutical composition comprising the crystalline compound (I) of claim 15.

19. A pharmaceutical composition comprising the crystalline compound (I) of claim 7.

20. A pharmaceutical composition comprising the crystalline compound (I) of claim 10.

* * * * *